(12) United States Patent
Everman et al.

(10) Patent No.: US 11,109,817 B2
(45) Date of Patent: Sep. 7, 2021

(54) SYSTEMS AND METHODS FOR MEASURING PHYSIOLOGICAL PARAMETERS

(71) Applicant: GMECI, LLC, Beavercreek, OH (US)

(72) Inventors: Bradford R Everman, Haddonfield, NJ (US); Brian Scott Bradke, Brookfield, VT (US)

(73) Assignee: GMECI, LLC, Beavercreek, OH (US)

( * ) Notice: Subject to any disclaimer, the term of this patent is extended or adjusted under 35 U.S.C. 154(b) by 124 days.

(21) Appl. No.: 16/265,953

(22) Filed: Feb. 1, 2019

(65) Prior Publication Data

US 2019/0167211 A1    Jun. 6, 2019

Related U.S. Application Data

(63) Continuation-in-part of application No. 16/012,713, filed on Jun. 19, 2018, now Pat. No. 10,765,380, (Continued)

(51) Int. Cl.
| | |
|---|---|
| *A61B 5/00* | (2006.01) |
| *A61B 5/0205* | (2006.01) |
| *A61B 5/1455* | (2006.01) |
| *G08B 21/04* | (2006.01) |
| *G09B 19/00* | (2006.01) |
| *G09B 9/10* | (2006.01) |
| *G09B 23/28* | (2006.01) |

(Continued)

(52) U.S. Cl.
CPC ............ *A61B 5/746* (2013.01); *A61B 5/0205* (2013.01); *A61B 5/14552* (2013.01); *A61B 5/486* (2013.01); *A61B 5/6803* (2013.01); *A61B 5/6814* (2013.01); *A61B 5/6822* (2013.01); *G08B 21/0453* (2013.01); *G09B 9/08* (2013.01); *G09B 9/10* (2013.01); *G09B 19/00* (2013.01); *G09B 23/28* (2013.01); *A61B 5/02416* (2013.01); *A61B 2560/0257* (2013.01); *A61B 2562/0219* (2013.01)

(58) Field of Classification Search
CPC combination set(s) only.
See application file for complete search history.

(56) References Cited

U.S. PATENT DOCUMENTS 6,498,942 B1    12/2002  Esenaliev
9,102,417 B1 *   8/2015  Young .................... B64D 45/00
(Continued)

FOREIGN PATENT DOCUMENTS

| KR | 1020050005661 A | 1/2005 |
| WO | 2011010295 A1 | 2/2001 |
| WO | 2011104888 A1 | 9/2011 |

*Primary Examiner* — Shirley X Jian
(74) *Attorney, Agent, or Firm* — Caldwell Intellectual Property Law, LLC

(57) ABSTRACT

A device for detecting physiological parameters is used to detect a degree of user hypoxemia in response to flight conditions; degree of hypoxemia may be used automatically to modify actions by a training device such as a reduced oxygen breathing device or centrifuge and generate feedback or modifications to training profiles for future use. Machine learning processes may be combined with sensor activity to discover relationships between maneuvers, environmental conditions, physiological parameters, and degrees of impairment to develop optimal flight or training plans.

20 Claims, 10 Drawing Sheets

Related U.S. Application Data which is a continuation-in-part of application No. 15/492,612, filed on Apr. 20, 2017, now Pat. No. 10,667,731.

(51) Int. Cl.
  *G09B 9/08* (2006.01)
  *A61B 5/024* (2006.01)

(56) References Cited

U.S. PATENT DOCUMENTS

| | | | | |
|---|---|---|---|---|
| 9,919,712 B1* | 3/2018 | Doyen | ............... | G16H 40/67 |
| 10,426,393 B2* | 10/2019 | Bosworth | ............... | B64D 45/00 |
| 10,595,758 B2* | 3/2020 | Buza | ............... | A61B 5/02416 |
| 2004/0206353 A1* | 10/2004 | Conroy, Jr. | ............... | A61B 5/417 |
| | | | | 128/204.23 |
| 2005/0202374 A1* | 9/2005 | Stepanek | ............... | A63B 23/08 |
| | | | | 434/37 |
| 2014/0123980 A1* | 5/2014 | Rissacher | ............... | A61M 16/0683 |
| | | | | 128/204.23 |
| 2014/0322675 A1* | 10/2014 | Bassovitch | ............... | G09B 9/10 |
| | | | | 434/59 |
| 2019/0090800 A1* | 3/2019 | Bosworth | ............... | B64C 13/02 |

* cited by examiner

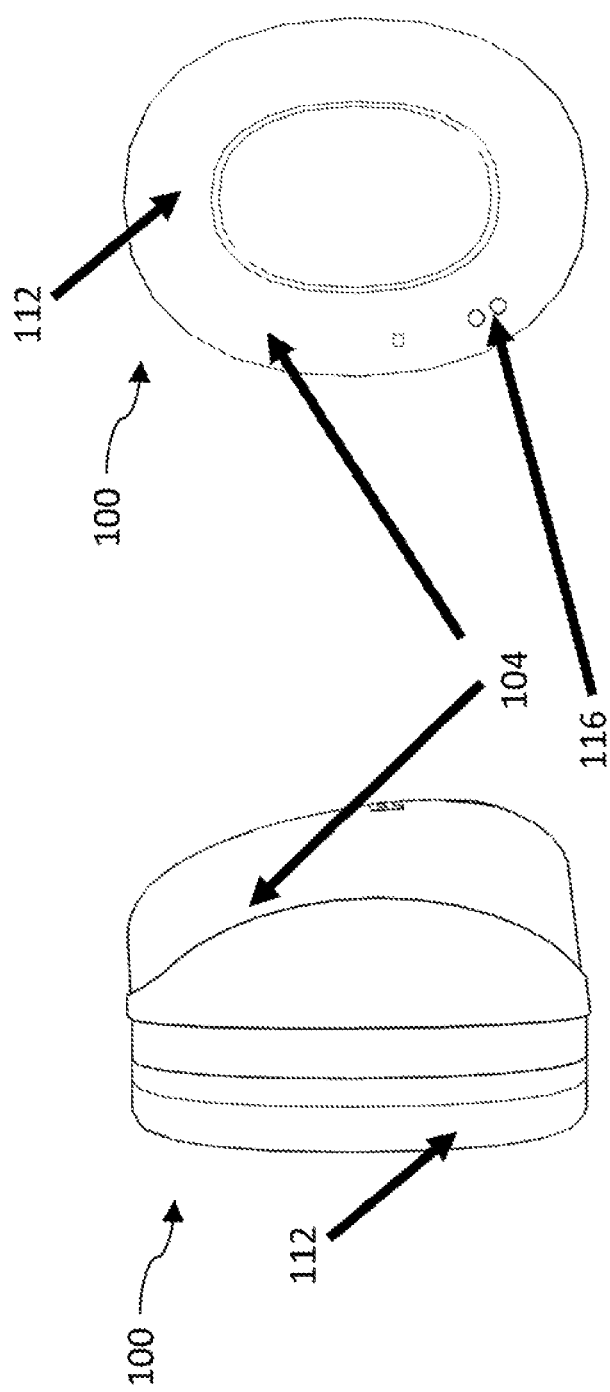

SYSTEMS AND METHODS FOR MEASURING PHYSIOLOGICAL PARAMETERS

RELATED APPLICATION DATA

This application is a continuation in part of U.S. nonprovisional patent application Ser. No. 16/012,713, filed on Jun. 19, 2018, and titled "SYSTEMS AND METHODS FOR MEASURING PHYSIOLOGICAL PARAMETERS", which is a continuation in part of U.S. nonprovisional patent application Ser. No. 15/492,612, filed on Apr. 20, 2017, and titled "HUMAN PERFORMANCE OXYGEN SENSOR." Each of U.S. nonprovisional patent application Ser. No. 16/012,713 and U.S. nonprovisional patent application Ser. No. 15/492,612 is incorporated herein by reference in its entirety.

FIELD OF THE INVENTION

This invention relates to physiological sensing devices, and in particular to systems and methods for measuring physiological parameters.

BACKGROUND

Blood oxygen saturation can determine a plurality of physical characteristics and ailments, including determining whether an individual is on the verge of losing consciousness. Typically, sensors measuring oxygenation are placed on the fingers or foreheads of patients and do not include a means of analyzing the data and alerting the user or a third party of whether an issue has been determined.

SUMMARY OF THE DISCLOSURE

According to an aspect, a device for training pilots using physiological sensor feedback for flight circumstances that cause hypoxemia, includes a housing configured to be mounted to an exterior body surface of a user. The device includes at least a physiological sensor attached to the housing and configured to detect at least a physiological parameter associated with hypoxemia. The device includes a training and feedback processor in communication with the at least a physiological sensor. The training and feedback processor is designed and configured to detect at least a flight condition having a causative association with hypoxemia, measure, using the at least a physiological sensor, at least a physiological parameter associated with hypoxemia, and determine, by the training and feedback processor, and based on the at least a physiological parameter, a degree of pilot hypoxemia. The device includes a user signaling device in communication with the training and feedback processor, the user signaling device configured to indicate the degree of pilot hypoxemia to at least a user.

In another aspect, a method of training pilots using physiological sensor feedback for flight circumstances that cause hypoxemia includes mounting a device for physiological sensor feedback to a user, the device further including a housing, at least a physiological sensor attached to the housing and configured to detect at least a physiological parameter associated with hypoxemia, and a training and feedback processor in communication with the at least a physiological sensor. The method includes detecting, by the training and feedback processor, at least a flight condition having a causative association with hypoxemia. The method includes measuring, using the at least a physiological sensor at least a physiological parameter associated with hypoxemia. The method includes determining, by the training and feedback processor, and based on the at least a physiological parameter, a degree of pilot hypoxemia. The method includes indicating, using a user signaling device, the degree of pilot hypoxemia to at least a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 shows a front view of a device according to an embodiment disclosed herein;

FIG. 3 shows a side view of a device according to an embodiment disclosed herein;

DETAILED DESCRIPTION

In an embodiment, devices and methods disclosed herein enable a system to detect physiological parameters such as blood oxygen level, blood pressure, and heart rate of a user through nonintrusive means. Sensors mounted in optimal locations on the head or neck of the user may detect physiological parameters accurately, minimizing interference in activities the user engages in while obtaining a clearer signal than otherwise would be possible. Embodiments of the disclosed device may provide users such as pilots, firemen, and divers who are operating under extreme circumstances with an early warning regarding potential crises such as loss of consciousness, affording the user a few precious extra seconds to avert disaster. Alarms may be provided to the user via bone-conducting transducers or by integration into displays the user is operating, increasing the likelihood that the user will notice the warning in time. Embodiments of devices, systems, and methods herein may enable training for pilots or other persons to function within physiological limitations imposed by their environment, such as hypoxemia imposed by altitude, high G forces and the like; training may further enable users to learn how to avoid total impairment, and to function under partial impairment.

Figure 1:
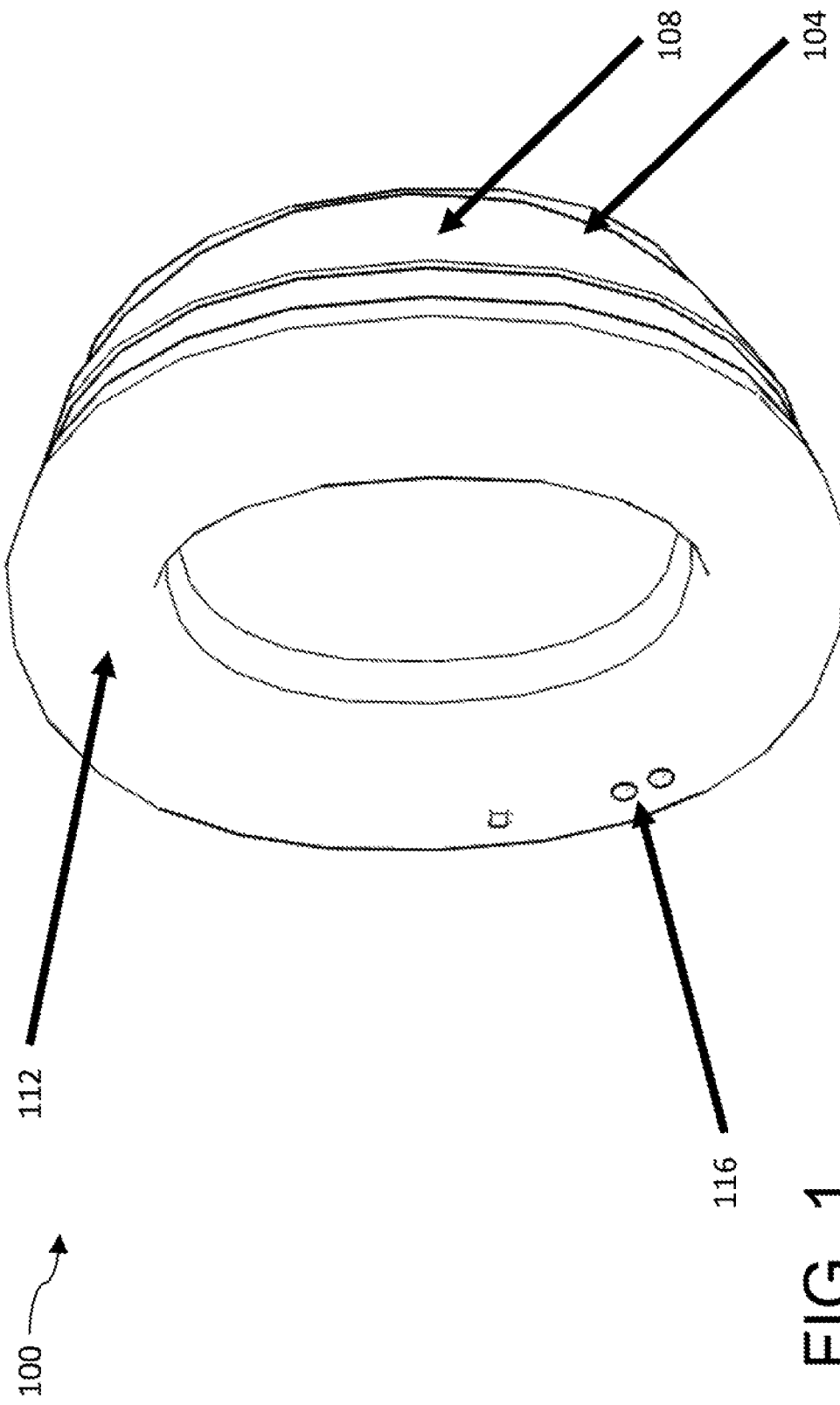
FIG. 1 shows a perspective view of a device according to an embodiment disclosed herein.
Figure 4:
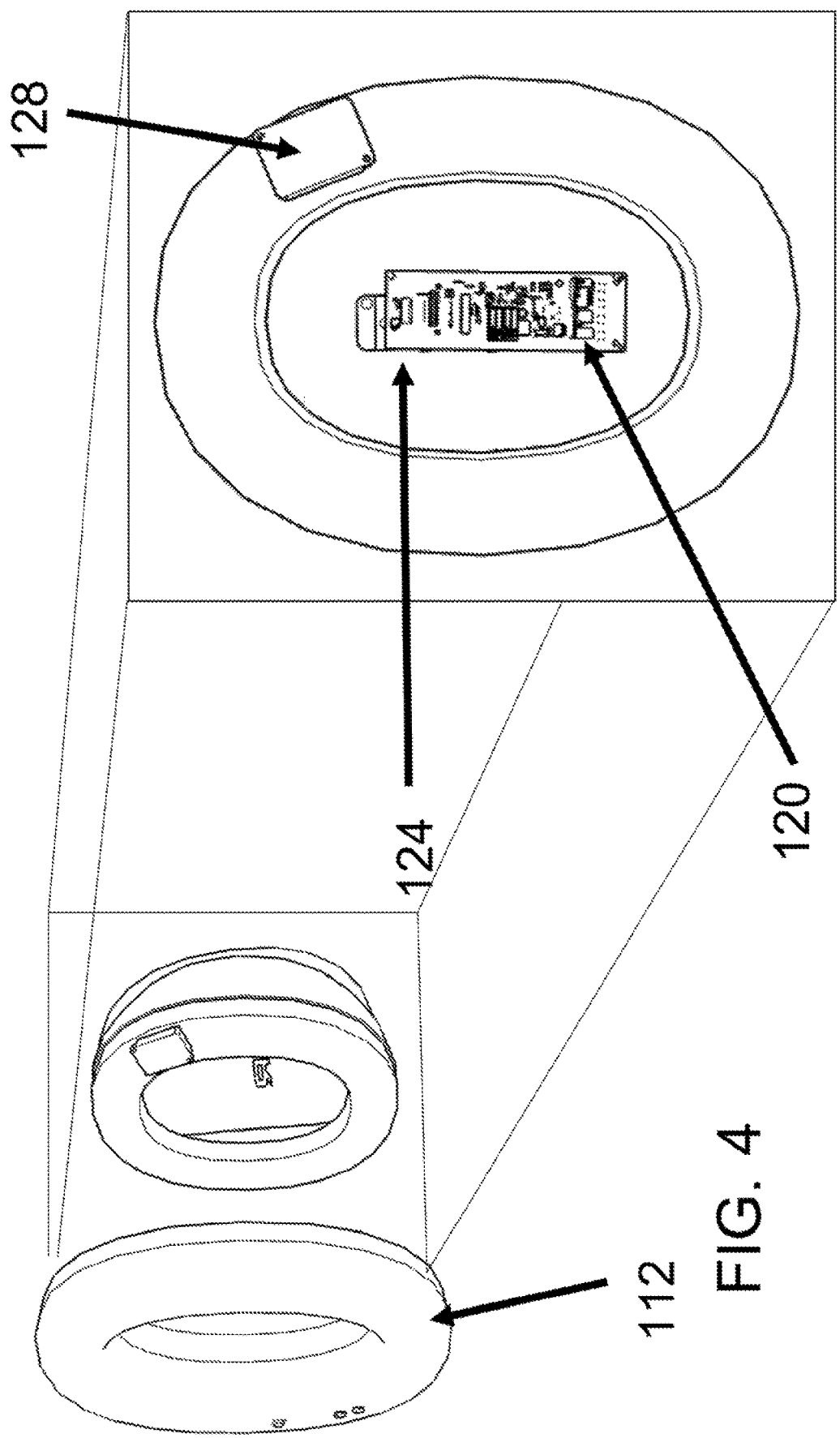
FIG. 4 shows a perspective view of a device according to an embodiment disclosed herein.

Referring now to FIGS. 1-5, an exemplary embodiment of a perspective view (FIG. 1), a side view (FIG. 2), a front view (FIG. 3), a perspective view (FIG. 4), and a front sectional view (FIG. 5) of a device for measuring physiological parameters 100 is illustrated. Referring now to FIG. 1, device for measuring physiological parameters 100 includes a housing 104. Housing 104 may be mounted to an exterior body surface of a user; exterior body surface may include, without limitation, skin, nails such as fingernails or toenails, hair, an interior surface of an orifice such as the mouth, nose, or ears, or the like. A locus on exterior body surface for mounting of housing 104 and/or other components of device may be selected for particular purposes as described in further detail below. Exterior body surface and/or locus may include an exterior body surface of user's head, face, or neck. Housing 104 may be constructed of any material or combination of materials, including without limitation metals, polymer materials such as plastics, wood, fiberglass, carbon fiber, or the like. Housing 104 may include an outer shell 108. Outer shell 108 may, for instance, protect elements of device 100 from damage, and maintain them in a correct position on a user's body as described in further detail below. Housing 104 and/or outer shell 108 may be shaped, formed, or configured to be inserted between a helmet worn on a head of the user and the exterior body surface; housing 104 and/or outer shell 108 may be shaped to fit between the helmet and the exterior body surface. As a non-limiting example, exterior body surface may be a surface, such as a surface of the head, face, or neck of user, which is wholly or partially covered by helmet, as described for example in further detail below. As a further non-limiting example, housing 104 may be formed to have a similar or identical shape to a standard-issue "ear cup" incorporated in an aviation helmet, so that housing 104 can replace ear cup after ear cup has been removed; in an embodiment, device 100 may incorporate one or more elements of ear-cup, including sound-dampening properties, one or more speakers or other elements typically used to emit audio signals in headsets or headphones, or the like. As a non-limiting example, device 100, housing 104, and/or shell may form a form-fit replacement for standard earcups found in military flight helmets. Shell may be rigid, where "rigid" is understood as having properties of an exterior casing typically used in an earcup, over-ear headphone, hearing protection ear covering, or the like; materials used for such a shell may include, without limitation, rigid plastics such as polycarbonate shell plastics typically used in helmets and hardhats, metals such as steel, and the like. Persons skilled in the art, upon reading the entirety of this disclosure, will understand "rigid" in this context as signifying sufficient resistance to shear forces, deformations, and impacts to protect electronic components as generally required for devices of this nature.

Still viewing FIGS. 1-5, housing 104 may include a seal 112 that rests against exterior body surface when housing 104 is mounted thereon. Seal 112 may be pliable; seal 112 may be constructed of elastomeric, elastic, or flexible materials including without limitation flexible, elastomeric, or elastic rubber, plastic, silicone including medical grade silicone, gel, and the like. Pliable seal 112 may include any combination of materials demonstrating flexible, elastomeric, or elastic properties, including without limitation foams covered with flexible membranes or sheets of polymer, leather, or textile material. As a non-limiting example, pliable seal 112 may include any suitable pliable material for a skin-contacting seal portion of an earcup or other device configured for placement over a user's ear, including without limitation any pliable material or combination of materials suitable for use on headphones, headsets, earbuds, or the like. In an embodiment, pliable seal 112 advantageously aids in maintaining housing 104 and/or other components of device 100 against exterior body surface; for instance, where exterior body surface has elastomeric properties and may be expected to flex, stretch, or otherwise alter its shape or position to during operation, pliable seal 112 may also stretch, flex, or otherwise alter its shape similarly under similar conditions, which may have the effect of maintaining seal 112 and/or one or more components of device 100 as described in greater detail below, in consistent contact with the exterior body surface. Seal 112 may be attached to housing 104 by any suitable means, including without limitation adhesion, fastening by stitching, stapling, or other penetrative means, snapping together or otherwise engaging interlocking parts, or the like. Seal 112 may be removably attached to housing 104, where removable attachment signifies attachment according to a process that permits repeated attachment and detachment without noticeable damage to housing 104 and/or seal 112, and without noticeable impairment of an ability to reattach again by the same process. As a non-limiting example, pliable seal 112 may be placed on an ear cup (for instance shown for exemplary purposes in FIG. 3) of the housing 104; pliable seal maybe formed of materials and/or in a shape suitable for use as an ear seal in an ear cup of a helmet, an over-ear headphone or hearing protection device, or the like. Persons skilled in the art, upon reviewing this disclosure in its entirety, will be aware of forms and material properties suitable for use as seal 112, including without limitation a degree and/or standard of pliability required and/or useful to function as a seal 112 in this context.

With continued reference to FIGS. 1-5, housing 104 may include, be incorporated in, or be attached to an element containing additional components to device 100. For instance, in an embodiment, housing 104 may include, be incorporated in, or be attached to a headset; headset may include, without limitation, an aviation headset, such as headsets as manufactured by the David Clark company of Worcester Mass., or similar apparatuses. In some embodiments, housing 104 is headset; that is, device 100 may be manufactured by incorporating one or more components into the headset, using the headset as a housing 104. As a further non-limiting example, housing 104 may include a mask; a mask as used herein may include any device or element of clothing that is worn on a face of user during operation, occluding at least a part of the face. Masks may include, without limitation, safety googles, gas masks, dust masks, self-contained breathing apparatuses (SCBA), self-contained underwater breathing apparatuses (SCUBA), and/or other devices worn on and at least partially occluding the face for safety, functional, or aesthetic purposes. Housing 104 may be mask; that is, device 100 may be manufactured by incorporating one or more elements or components of device 100 in or on mask, using mask as housing 104. Housing 104 may include, be incorporated in, or be attached to an element of headgear, defined as any element worn on and partially occluding a head or cranium of user. Headgear may wholly or partially occlude user's face and thus also include a mask; headgear may include, for instance, a fully enclosed diving helmet, space helmet or helmet incorporated in a space suit, or the like. Headgear may include a headband, such as without limitation a headband of a headset, which may be an aviation headset. Headgear may include a hat. Headgear may include a helmet, including a motorcycle helmet, a helmet used in automobile racing, any helmet used in any military process or operation, a construction "hardhat," a bicycle helmet, or the like. In an embodiment, housing 104 is shaped to conform to a particular portion of user anatomy when placed on exterior body surface; when placed to so conform, housing 104 may position at least a sensor and/or user-signaling device 128 in a locus chosen as described in further detail below. For instance, where housing 104 is incorporated in a helmet, mask, earcup or headset, housing 104 may be positioned at a particular portion of user's head when helmet, mask, earcup or headset is worn, which may in turn position at least a sensor and/or user-signaling device 128 at a particular locus on user's head or neck.

Continuing to refer to FIGS. 1-5, device 100 includes at least a physiological sensor 116. At least a physiological sensor 116 is configured to detect at least a physiological parameter and transmit an electrical signal as a result of the detection; transmission of an electrical signal, as used herein, includes any detectable alternation of an electrical parameter of an electrical circuit incorporating at least a physiological sensor 116. For instance, at least a physiological sensor 116 may increase or reduce the impedance and/or resistance of a circuit to which at least a physiological sensor 116 is connected. At least a physiological sensor 116 may alter a voltage or current level, frequency, waveform, amplitude, or other characteristic at a locus in circuit. Transmission of an electrical signal may include modulation or alteration of power circulating in circuit; for instance transmission may include closing a circuit, transmitting a voltage pulse through circuit, or the like. Transmission may include driving a non-electric signaling apparatus such as a device for transmitting a signal using magnetic or electric fields, electromagnetic radiation, optical or infrared signals, or the like.

Still referring to FIGS. 1-5, at least a physiological parameter, as used herein, includes any datum that may be captured by a sensor, and describing a physiological state of user. At least a physiological parameter may include at least a circulatory and/or hematological parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse and/or blood oxygen level (for instance by detecting plethysmograph amplitude), pulse rate (for instance by detecting plethysmograph frequency), heart rate variability and rhythm (for instance by tracking pulse rate and other factors over time), and blood pressure, among other things. At least a physiological sensor may be configured to detect at least a hematological parameter of at least a branch of a carotid artery; at least a physiological parameter may be positioned to capture the at least a hematological parameter by placement on a location of housing that causes at least a physiological sensor to be placed in close proximity to the at least a branch; for instance, where housing is configured to be mounted to a certain location on a user's cranium, and in a certain orientation, such as when housing forms all or part of a helmet, headset, mask, element of headgear, or the like, at least a physiological sensor may include a sensor so positioned on the housing or an extension thereof that it will contact or be proximate to a locus on the user's skin under which the at least a branch runs. As a non-limiting example, where device 100 forms an earcup or earphone, at least a physiological sensor 116 may include a sensor disposed on or embedded in a portion of the earcup and/or earphone contacting a user's skin over a major branch of the external carotid artery that runs near or past the user's ear.

In an embodiment, and still viewing FIGS. 1-5, detection of hematological parameters of at least a branch of a carotid artery may enable device 100 to determine hematological parameters of a user's central nervous system with greater accuracy than is typically found in devices configured to measure hematological parameters. For instance, a blood oxygen sensor placed on a finger or other extremity may detect low blood oxygen levels in situations in which the central nervous system is still receiving adequate oxygen, because a body's parasympathetic response to decreasing oxygen levels may include processes whereby blood perfusion to the appendages is constricted in order to sustain higher oxygen levels to the brain; in contrast, by directly monitoring the oxygenation of a major branch of the external carotid artery, the measurement of oxygenation to the central nervous system may be more likely to achieve a more accurate indication of oxygen saturation than a peripheral monitor. Use of the carotid artery in this way may further result in a more rapid detection of a genuine onset of hypoxemia; as a result, a person such as a pilot that is using device 100 may be able to function longer under conditions tending to induce hypoxemia, knowing that an accurate detection of symptoms may be performed rapidly and accurately enough to warn the user. This advantage may both aid in and be augmented by use with training processes as set forth in further detail below.

With continued reference to FIGS. 1-5, at least a physiological sensor 116 may include a hydration sensor; hydration sensor may determine a degree to which a user has an adequate amount of hydration, where hydration is defined as the amount of water and/or concentration of water versus solutes such as electrolytes in water, in a person's body. Hydration sensor may use one or more elements of physiological data, such as sweat content and/or hematological parameters detected without limitation using plethysmography, to determine a degree of hydration of a user; degree of hydration may be associated with an ability to perform under various circumstances. For instance, a person with adequate hydration may be better able to resist the effects of hypoxemia in high-altitude and/or high-G for longer or under more severe circumstances, either because the person's body is better able to respond to causes of hypoxemia and delay onset, or because the person is better able to cope with diminished blood oxygen; this may be true of other conditions and/or physiological states detected using at least a physiological sensor 116, and may be detected using heuristics or relationships derived, without limitation, using machine learning and/or data analysis as set forth in further detail below.

Still referring to FIGS. 1-5, at least a physiological sensor 116 may include a volatile organic compound (VOC) sensor. VOC sensor may sense VOCs, including ketones such as acetone; a user may emit ketones in greater quantities when undergoing some forms of physiological stress, including without limitation hypoglycemia resulting from fasting or overwork, which sometimes results in a metabolic condition known as ketosis. As a result, detections of higher quantities of ketones may indicate a high degree of exhaustion or low degree of available energy; this may be associated with a lessened ability to cope with other physiological conditions and/or parameters that may be detected by or using at least a physiological sensor 116, such as hypoxemia, and/or environmental stressors such as high altitude or G-forces. Such associations may be detected or derived using data analysis and/or machine learning as described in further detail below.

With continued reference to FIGS. 1-5, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Still referring to FIGS. 1-5, at least a physiological sensor 116 may include an optical sensor, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. FIG. 6 illustrates an exemplary embodiment of a NIRS 600 against an exterior body surface, which may include skin. NIRS 600 may include a light source 604, which may include one or more light-emitting diodes (LEDs) or similar element. Light source 604 may, as a non-limiting example, convert electric energy into near-infrared electromagnetic signals. Light source 604 may include one or more lasers. NIRS 600 may include one or more detectors 608 configured to detect light in the near-infrared spectrum. Although the wavelengths described herein are infrared and near-infrared, light source 604 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 608 may include, without limitation, charge-coupled devices (CCDs) biased for photon detection, indium gallium arsenide (InGaAs) photodetectors, lead sulfide (PbS) photodetectors, or the like. NIRS 600 may further include one or more intermediary optical elements (not shown), which may include dispersive elements such as prisms or diffraction gratings, or the like. In an embodiment, NIRS 600 may be used to detect one or more circulatory parameters, which may include any detectable parameter further comprises at least a circulatory parameter. At least a physiological sensor 116 may include at least two sensors mounted on opposite sides of user's cranium.

Referring again to FIGS. 1-5, at least a physiological sensor 116 may include a neural activity sensor. A neural activity sensor, as used herein, includes any sensor disposed to detect electrical or magnetic phenomena generated by neurons, including cranial neurons such as those located in the brain or brainstem. Neural activity sensor may include an electroencephalographic sensor. Neural activity sensor may include a magnetoencephalographic sensor. In an embodiment, neural activity sensor may be configured to detect neural oscillations. At least a sensor may include an eye-tracking sensor, such as one or more cameras for tracking the eyes of user. Eye-tracking sensor may include, as a non-limiting example, one or more electromyographic (EMG) sensors, which may detect electrical activity of eye muscles; electrical activity may indicate activation of one or more eye muscles to move the eye and used by a circuit such as an alert circuit as described below to determine a movement of user's eyeball, and thus its current location of focus.

Continuing to refer to FIGS. 1-5, device 100 may communicate with one or more physiological sensors that are not a part of device 100; one or more physiological sensors may include any sensor suitable for use as at least a physiological sensor 116 and/or any other physiological sensor. Communication with physiological sensors that are not part of device may be accomplished by any means for wired or wireless communication between devices and/or components as described herein. Device may detect and/or measure at least a physiological parameter using any suitable combination of at least a physiological sensor and/or physiological sensors that are not a part of device 100. Device 100 may combine two or more physiological parameters to detect a physiological condition and/or physiological alarm condition. For instance, and without limitation, where device 100 is configured to detect hypoxic incapacitation and/or one or more degrees of hypoxemia as described in further detail below, device 100 may perform such determination using a combination of heart rate and blood oxygen saturation, as detected by one or more sensor as described above.

Still viewing FIGS. 1-5, at least a physiological sensor 116 may be attached to housing 104; attachment to housing 104 may include mounting on an exterior surface of housing 104, incorporation within housing 104, electrical connection to another element within housing 104, or the like. Alternatively or additionally, at least a physiological sensor 116 may include a sensor that is not attached to housing 104 or is indirectly attached via wiring or the like. As a non-limiting example, at least a physiological sensor 116 and/or one or more components thereof may be coupled to the pliable seal 112. In an embodiment, at least a physiological sensor 116 may be contacting exterior body surface; this may include direct contact with the exterior body surface, or indirect contact for instance through a portion of seal 112 or other components of device 100. In an embodiment, at least a physiological sensor 116 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. At least a physiological sensor 116 may contact a locus having little or no hair on top of skin. At least a physiological sensor 116 may contact a locus near to a blood vessel, such as a locus where a large artery such as the carotid artery or a branch thereof, or a large vein such as the jugular vein, runs near to skin or bone at the location; in an embodiment, such a position may permit at least a physiological sensor 116 to detect circulatory parameters as described above.

Figure 7:
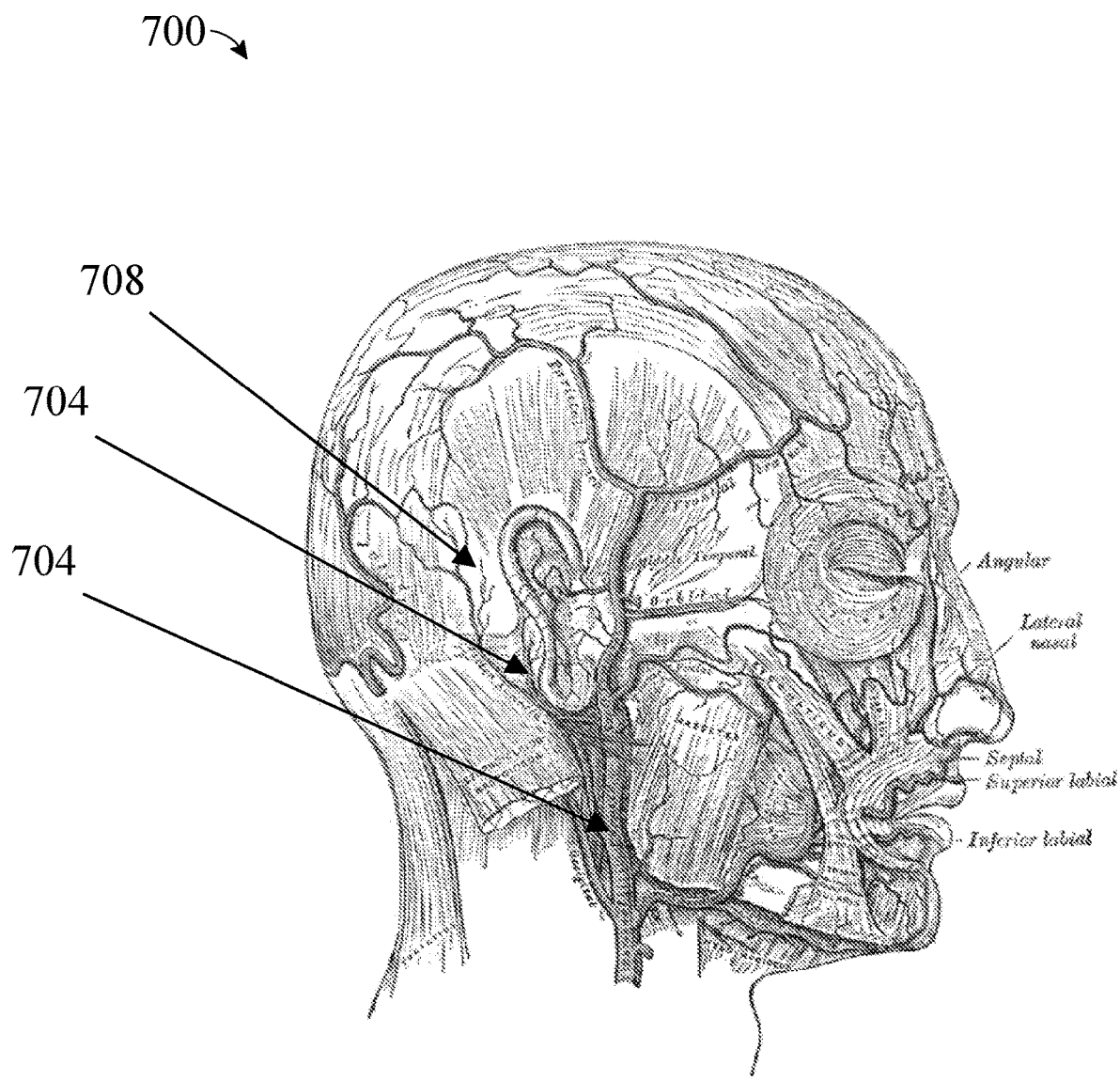
FIG. 7 is a schematic diagram of some aspects of user cranial anatomy in an embodiment.

Referring now to FIG. 7, a schematic diagram of anatomy of a portion of a user cranium 700 is illustrated for exemplary purposes. At least a physiological sensor 116 may, for instance, be placed at or near to a locus adjacent to a branch 704 of a carotid artery, which may be a branch of an exterior carotid artery. At least a physiological sensor 116 may be placed at a location 708 where substantially no muscle is found between a user's skin and bone; such a location may be found, for instance, near to the user's neck behind the ear. In an embodiment, at least a physiological sensor may be placed in a locus that is both adjacent to a branch 704 of a carotid artery and has substantially no muscle between skin and bone. In an embodiment, measurement of at least a physiological parameter, including without limitation pulse oxygenation and/or pulse rate as described in further detail below, on a particular portion of the cranium may eliminate interfering factors such as sweat and movement artifact; measurement above the neck may further eliminate measurement issues experienced at the extremities (finger, wrist) due to temperature variation, movement and blood pooling under G. Where multiple physiological sensors of at least a physiological sensor 116 are used, at least two sensors may be placed at two locations on a user's cranium; for instance, two sensors, one on each side of the cranium, may provide validation of consistent data, and assures a high capture rate of data in flight. Two sensors may be so placed, as noted elsewhere in this disclosure, by form and/or configuration of housing 104; for instance, housing 104 may include two earcups or other over-ear devices as described above.

As a non-limiting example of placement of at least a physiological sensor 116, and as illustrated for exemplary purposes in FIGS. 1-5, at least a physiological sensor 116 may include a sensor mounted on an edge of an earcup, and so positioned that placement of earcup over user's ear places sensor in contact with user's head just behind the ear at a local skeletal eminence, with substantially no muscle tissue between skin and bone and a branch of the carotid artery nearby for detection of circulatory parameters. Similarly, where housing 104 includes a mask as described above, a sensor of at least a physiological sensor 116 may be disposed within mask at a location that, when mask is worn, places sensor against a forehead of user.

Still viewing FIGS. 1-5, where at least a physiological sensor 116 includes a neural activity sensor, at least a physiological sensor 116 may include one or more sensors placed in locations suitable for detection of neural activity, such as on upper surfaces of a cranium of user, or similar locations as suitable for EEG or MEG detection and measurement.

With continued reference to FIGS. 1-5, device 100 includes a training and feedback processor 120 in communication with the at least a physiological sensor. As used herein, a device, component, or circuit is "in communication" where the device, component, or circuit is able to receive data from and/or transmit data to another device, component, or circuit. In an embodiment, devices are placed in communication by electrically coupling at least an output of one device, component, or circuit to at least an input of another device, component, or circuit. Devices may further be placed in communication by creating an optical, inductive, or other coupling between two or more devices. Devices in communication may be placed in near field communication with one another. Two or more devices may be in communication where the two or more devices are configured to send and/or receive signals to or from each other. Placement of devices in communication may include direct or indirect connection and/or transmission of data; for instance, two or more devices may be connected or otherwise in communication by way of an intermediate circuit. Placement of devices in communication with each other may be performed via a bus or other facility for intercommunication between elements of a computing device as described in further detail below in reference to FIG. 11. Placement of devices in communication with each other may include fabrication together on a shared integrated circuit and/or wafer; for instance, and without limitation, two or more communicatively coupled devices may be combined in a single monolithic unit or module.

With continued reference to FIGS. 1-5, training and feedback processor 120 may be constructed according to any suitable process or combination of processes for constructing an electrical circuit; for instance, and without limitation, training and feedback processor 120 may include a printed circuit board. Training and feedback processor 120 may include a battery or other power supply; where training and feedback processor 120 is integrated in one or more other systems as described in further detail below, training and feedback processor 120 may draw electrical power from one or more circuit elements and/or power supplies of such systems. Training and feedback processor 120 may include a memory; memory may include any memory as described below in reference to FIG. 11. Training and feedback processor 120 may include one or more processors as described in further detail below in reference to FIG. 11, including without limitation a microcontroller or low-power microprocessor. In an embodiment, memory may be used to store one or more signals received from at least a physiological sensor 116.

Figure 5:
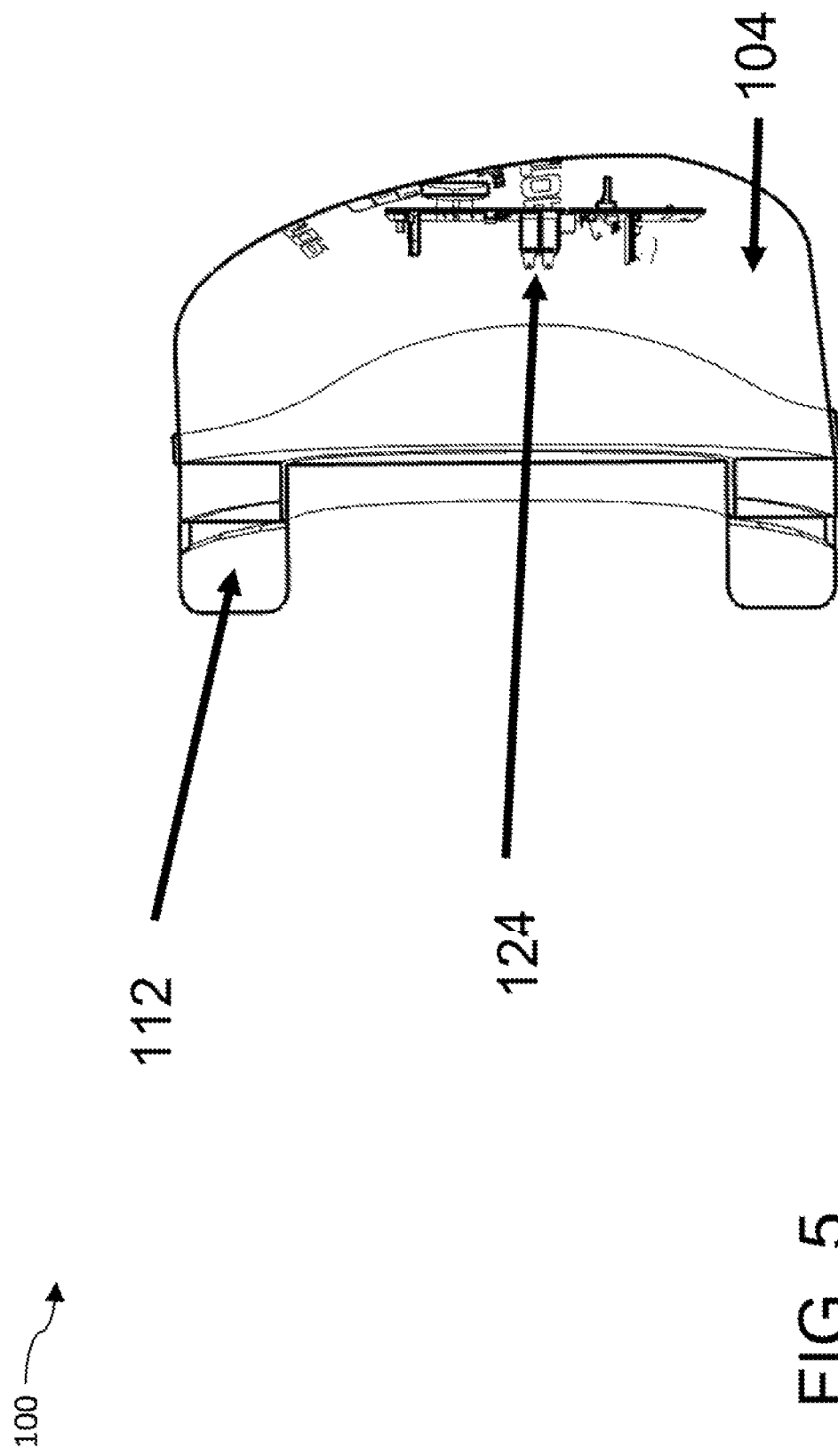
FIG. 5 shows a front sectional view of a device according to an embodiment disclosed herein.
Figure 6:
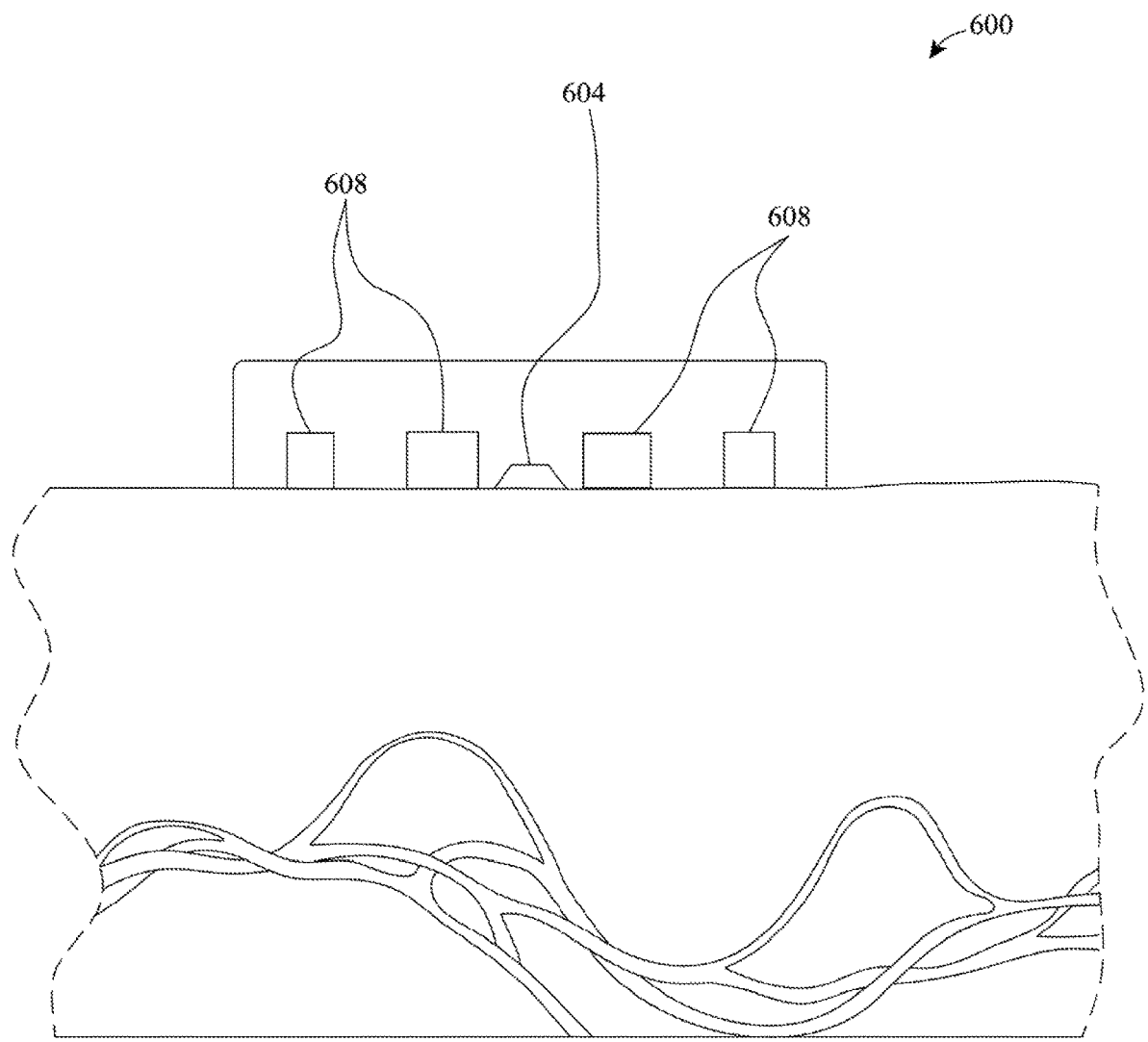
FIG. 6 is a schematic illustration of an exemplary embodiment of a near-infrared spectroscopy sensor.

Still referring to FIGS. 1-5, training and feedback processor 120 may be in communication with at least an environmental sensor 124; at least an environmental sensor 124 may be any sensor configured to detect at least an environmental parameter, defined herein as a parameter describing non-physiological data concerning user or surroundings of user, such as acceleration, carbon monoxide, or the like. At least an environmental sensor 124 may include at least a motion sensor, including without limitation one or more accelerometers, gyroscopes, magnetometers, or the like; at least a motion sensor may include an inertial measurement unit (IMU). At least an environmental sensor 124 may include at least a temperature sensor. At least an environmental sensor 124 may include at least an air quality sensor, such as without limitation a carbon monoxide sensor, or other sensor of any gas or particulate matter in air. At least an environmental sensor may include an atmospheric oxygen sensor, an oxygen flow meter, and/or a mask oxygen/$CO_2$ sensor. At least an environmental sensor 124 may include at least a barometric sensor. At least an environmental sensor 124 may include a pressure sensor, for instance to detect air or water pressure external to user. Training and feedback processor 120 may be attached to housing 104, for instance by incorporation within housing 104; as a non-limiting example and as shown in FIG. 5, the training and feedback processor 120 may be housed along an inner wall of the housing 104. Training and feedback processor 120 may be attached to an exterior of housing 104. According to an embodiment, a covering may be placed over housing 104, fully enclosing the training and feedback processor 120 within the housing 104; the enclosure may include a plastic, a metal, a mesh-type material, and/or any other suitable material. Training and feedback processor 120 may be in another location not attached to or incorporated in housing 104. Training and feedback processor 120 may be incorporated into and/or connected to one or more additional elements including any elements incorporating or connected to user signaling devices as described in further detail below. As an alternative to storage of one or more parameter values such as physiological parameters or environmental parameters in memory, alert circuit may transmit the data to one or more remote storage mediums through one or more wired and/or wireless means.

Still viewing FIGS. 1-5, training and feedback processor 120 may be configured to receive at least a signal from the at least a physiological sensor 116, generate an alarm as a function of the at least a signal, and to transmit the alarm to a user-signaling device 128 in communication with the training and feedback processor 120. Training and feedback processor 120 may periodically sample data from at least a sensor; in a non-limiting example, data may be sampled 75 times per second. In an embodiment, alarm is generated upon detection of any signal at all from at least a physiological sensor 116; for instance, at least a physiological sensor 116 may be configured only to signal training and feedback processor 120 upon detection of a problematic or otherwise crucial situation. Alternatively or additionally, training and feedback processor 120 is further configured to detect a physiological alarm condition and generate the alarm as a function of the physiological alarm condition. In an embodiment, a physiological alarm condition includes any physiological condition of user that may endanger user or impair user's ability to perform an important task; as a non-limiting example, if user is flying an aircraft and user's physiological condition is such that user is unable to concentrate, respond rapidly to changing conditions, see or otherwise sense flight controls or conditions, or otherwise successfully operate the aircraft within some desired tolerance of ideal operation, a physiological alarm condition may exist, owing to the possibility of inefficient or dangerous flight that may result. Similarly, if user's physiological condition indicates user is experiencing or about to experience physical harm, is losing or is about to lose consciousness, or the like, a physiological alarm condition may exist.

Still referring to FIGS. 1-5, training and feedback processor 120 may be configured to perform any embodiment of any method and/or method step as described in this disclosure. For instance, and without limitation, training and feedback processor 120 may be designed and configured to detect at least a flight condition having a causative association with hypoxemia, measure, using at least a physiological sensor, at least a physiological parameter associated with hypoxemia, and determine, by the training and feedback processor 120, and based on the at least a physiological parameter, a degree of pilot hypoxemia.

In an embodiment, and still viewing FIGS. 1-5, detection of a physiological alarm condition may include comparison of at least a physiological parameter to a threshold level. For instance, and without limitation, detection of the physiological alarm condition further comprises determination that the at least a physiological parameter is falling below a threshold level; as an example, blood oxygen levels below a certain cutoff indicate an imminent loss of consciousness, as may blood pressure below a certain threshold. Similarly detection of a physiological alarm condition may include detection of alpha wave activity falling below a certain point, which may indicate entry into early stages of sleep or a hypnogogic state, and/or entry into unconsciousness. Comparison to threshold to detect physiological alarm condition may include comparison of at least a physical parameter to a value stored in memory, which may be a digitally stored value; alternatively or additionally comparison may be performed by analog circuitry, for instance by comparing a voltage level representing at least a physical parameter to a reference voltage representing the threshold, by means of a comparator or the like. Threshold may represent or be represented by a baseline value. Detection of a physiological alarm condition may include comparison to two thresholds; for instance, detection that incapacitation and/or loss of consciousness due to hypoxemia is imminent may include detection that a user's heart rate has exceeded one threshold for heart rate and simultaneous or temporally proximal detection that blood oxygen saturation has fallen below a second threshold. Threshold or thresholds used for such comparison to detect a physiological alarm condition may include universal and/or default thresholds. For instance, device 100 may be set, prior to use with a particular individual, with thresholds corresponding to a typical user's response to physiological conditions. For instance, device 100 may initially store a threshold in memory of device 100 of 70% blood oxygen saturation, as indicating that a typical user is likely incapacitated by hypoxemia when blood oxygen saturation of that user, including blood oxygen saturation in a cranial vessel such as a branch of a carotid artery, has fallen below 70%; however, data gathered regarding a particular user may indicate that the particular user is only likely to be incapacitated at 65% blood oxygen saturation and/or that the particular user is likely to be incapacitated at 75% blood oxygen saturation, and threshold may be modified in memory accordingly.

Still referring to FIGS. 1-5, in an embodiment, a single physiological parameter and/or combination of physiological parameters may be associated with a plurality of thresholds indicating a plurality of degrees of physiological conditions, such as degrees of incapacitation. As a non-limiting example, a plurality of thresholds may be stored regarding blood oxygen saturation, such as without limitation a first threshold indicating a possible saturation problem, a second indicating a degree of blood oxygen saturation consistent with some degree of performance degradation on the part of the user, and a third threshold indicating that incapacitation is likely. By way of illustration, and without limitation, default or factory-set thresholds may include a first threshold triggered upon a user crossing into 80-90% blood oxygen saturation, indicating "saturation possible problem," a second threshold upon the user crossing into 70-80% saturation, indicating "Performance degraded," and a third threshold upon the user crossing into <70% saturation indicating "incapacitation likely," while 90-100% saturation may indicate a normal amount of blood oxygen saturation. Generally, multiple thresholds may be set just above physiologically-relevant levels corresponding to onset of symptoms, cognitive impairment, and total incapacitation for a very-accurate, user-specific warning tone. User-specific thresholds at any tier or degree of incapacitation may be set and/or adjusted according to an iterative process, where users define thresholds, and/or the system finds user thresholds based on, as a non-limiting example, user-specific training and/or sortie data. Determination that of an alarm state such as alarm states associated with one or more thresholds as described above may alternatively or additionally be performed without a threshold comparison, for instance by identifying a correlation of two or more sensor data determined, for instance using machine learning as described below, to be associated with entry into such one or more alarm states; as a non-limiting example, detection of imminent incapacitation and/or unconsciousness due to hypoxemia may be accomplished by detecting a simultaneous or temporally correlated increase in heart rate and decrease in blood oxygen saturation. Combinations or associations of sensor data may further involve measuring several human performance metrics including SPO2, Pulse Rate, and full plethysmograph as well as environmental sensor data such as flight conditions for full characterization and correlation of human performance in flight, for instance as described in further detail below.

Still referring to FIGS. 1-5, detection of physiological alarm condition may include comparing at least a physiological parameter to at least a baseline value and detecting the physiological alarm condition as a function of the comparison. At least a baseline value may include a number or set of numbers representing normal or optimal function of user, a number or set of numbers representing abnormal or suboptimal function of user, and/or a number or set of numbers indicating one or more physiological parameters demonstrating a physiological alarm condition. At least a baseline value may include at least a threshold as described above. In an embodiment, at least a baseline value may include a typical user value for one or more physiological parameters. For example, and without limitation, at least a baseline value may include a blood oxygen level, blood pressure level, pulse rate, or other circulatory parameter, or range thereof, consistent with normal or alert function in a typical user; at least a baseline value may alternatively or additionally include one or more such values or ranges consistent with loss of consciousness or impending loss of consciousness in a typical user. Similarly, at least a baseline value may include a range of neural oscillations typically associated in users with wakeful or alert states of consciousness, and/or a range of neural oscillations typically associated with sleeping or near-sleeping states, loss of consciousness or the like. Training and feedback processor 120 may receive a typical user value and using the typical user value as the baseline value; for instance, training and feedback processor 120 may have typical user value entered into memory of training and feedback processor 120 by a user or may receive typical user value over a network or from another device. At least a baseline value may be maintained in any suitable data structure, including a table, database, linked list, hash table, or the like.

Continuing to refer to FIGS. 1-5, typical user value may include a user value matched to one or more demographic facts about user. For instance, a pulse rate associated with loss of consciousness in women may not be associated with loss of consciousness in men, or vice-versa; where user is a woman, the former pulse rate may be used as a baseline value for pulse rate. Baseline value may similarly be selected using a typical value for persons matching user's age, sex, height, weight, degree of physical fitness, physical test scores, ethnicity, diet, or any other suitable parameter. Typical user baseline value may be generated by averaging or otherwise aggregating baseline values calculated per user as described below; for instance, where each user has baseline values established by collection of physiological parameters using devices such as device 100, such values may be collected, sorted according to one or more demographic facts, and aggregated to produce a typical user baseline value to apply to user. Still referring to FIGS. 1-5, baseline value may be created by collection and analysis of at least a physiological parameter; collection and/or analysis may be performed by training and feedback processor 120 and/or another device in communication with training and feedback processor 120. For instance, receiving a baseline value may include collecting a plurality of samples of the at least a physiological parameter and calculating the baseline value as a function of the plurality of samples. Device 100 may continuously or periodically read or sample signals from at least a physiological sensor 116, recording the results; such results may be timestamped or otherwise co-associated, such that patterns concerning physiological parameters may be preserved, detected, and/or analyzed. For example and without limitation, user pulse rate and/or blood pressure may vary in a consistent manner with blood oxygen level; user blood pressure and/or pulse rate may further vary in a consistent manner with brain wave activity. Additional information from other sensors may similarly collected to form baseline value; for instance, where user is operating a machine, such as an aircraft, data concerning operation, such as flight control data, may be collected and associated with at least a physiological parameter. As a non-limiting example, user's reaction time when operating an aircraft may be measurably slower when user's blood pressure is below a certain amount, while showing no particular change for variations in blood pressure above that amount. Additional information may further be provided by user and/or another person evaluation user behavior and/or performance. For example, during test flights or other operation of an aircraft where user and/or aircraft may be observed, user, a supervisor, or another observer may record information such as the user's performance, the user's feelings or apparent state of health, the performance of the aircraft, and the like. Some factors that may be relatively objectively monitored regarding the overall state of health experience by the user may include how many times the user has to use "anti-G" breathing exercises, or similar activities. In an embodiment, data is received from user and/or observers via numerical ratings, or selections of buttons or other entry devices that map to numerical ratings. Alternatively or additionally, entries may be formed using one or more text entries; text entries may be mapped to numerical ratings or the like using, as a non-limiting example, natural language analysis, textual vector analysis, or the like. Plurality of physiological parameters and/or user entries and other entries may be collected over time, during, for instance a series of routine activities by user.

Continuing to refer to FIGS. 1-5, baseline value may be generated by collection of data from at least an environmental sensor 124. For instance, each set of one or more physiological parameters taken at a particular moment, or over a particular period of time, may be linked in memory to one or more environmental parameters, including without limitation motion-sensor data, air quality data, and the like. This may be used by device 100, as a non-limiting example, to collect relationships between environmental parameters and physiological parameters, such as a relationship between localized or systemic blood pressure, G-forces, and state of consciousness of a user in an aircraft, or a relationship between quality of neural oscillations and external water pressure in a diver. This in turn may be used to produce additional baseline information as described in further detail below. As further examples, relationships determined to achieve baseline values may include comparisons of heart rate, heart rate increase and heart rate recovery are easily compared to scientifically derived norms established in academia and professional athletics. Relationships may include correlation of blood oxygen saturation, heart rate and heart rate variability. These metrics may be useful for objectively determining deliberate risk levels associated with human performance, for instance using population data and/or machine learning as described in further detail below. In an embodiment, a baseline study of each individual performance against known conditions, such as in the Restricted Oxygen Breathing Device, may be performed prior to use of device 10; a purpose of the baseline evaluation may be to assess how each individual responds to specific conditions. Such a response may be used to both validate the data to draw usable conclusions, as well as to calibrate the alarm system to provide meaningful data while reducing the incidence of false alarms, for instance by setting and/or adjusting default threshold levels as described above.

With continued reference to FIGS. 1-5, plurality of physiological parameters, plurality of environmental parameters, and/or user-entered data may be aggregated, either independently or jointly. For instance, device 100 may calculate an average level, for one or more parameters of at least a physiological parameter, associated with normal or optimal function, health, or performance of user; a standard deviation from the average may also be calculated. This may be used, e.g., to generate an alarm indicating that, for instance, a given physiological parameter has recently shifted more than a threshold amount from its average value. Threshold amount may be determined based on amounts by which a typical user may deviate from average amount before experiencing discomfort, loss of function, or loss of consciousness. Threshold amount may be set as some multiple of standard deviations, as calculated from sensed physiological parameters; for instance, two or more standard deviations from an average value for a given detected physiological parameter may trigger an alarm.

Alternatively or additionally, and still referring to FIGS. 1-5, aggregation may include aggregation of relationships between two or more parameters. For instance, and without limitation, aggregation may calculate a relationship between a first physiological parameter of the at least a physiological parameter and a second physiological parameter of the at least a physiological parameter; this relationship may be calculated, as a non-limiting example, by selecting a first parameter as a parameter associated with a desired state for the user and a second parameter known or suspected to have an effect on the first parameter. For example, first parameter may be blood oxygen level, and second parameter may be blood pressure, such as localized blood pressure in a cranial region; a reduction in cranial blood pressure may be determined to be related to a reduction in cranial blood oxygen level, which in turn may be related to loss of consciousness or other loss of function in user or in a typical user. As another example, aggregation may calculate a relationship between a physiological parameter of the at least a physiological parameter and an environmental parameter. For example, blood oxygen level may be inversely related to an amount of acceleration or G force a user is experiencing in an aircraft; this relationship may be directly calculated from those two values, or indirectly calculated by associating the amount of acceleration or G force with a degree of decrease in cranial blood pressure, which may then be related to blood oxygen levels. Aggregation may calculate a relationship between at least a physiological parameter and user-entered data; for instance, people observing user may note losses of performance or apparent function at times associated with a certain degree of decrease in blood oxygen level or some other physiological parameter. The relationships may be between combinations of parameters: for instance, loss of function may be associated with an increase in G forces coupled with a decrease in pulse rate, or a decrease in blood oxygen coupled with a decrease in alpha waves, or the like.

Still referring to FIGS. 1-5, relationships between two or more of any of physiological parameters, environmental parameters, and/or user-entered parameters may be determined by one or more machine-learning algorithms. Machine-learning algorithms as used herein are processes executed by computing devices to improve accuracy and efficiency of other processes performed by the computing devices, or detect relationships between data sets, through statistical or mathematical measures of accuracy and efficiency. Machine learning may function by measuring a difference between predicted answers or outputs and goal answers or outputs representing ideal or "real-world" outcomes the other processes are intended to approximate. Predicted answers or outputs may be produced by an initial or intermediate version of the process to be generated, which process may be modified as a result of the difference between predicted answers or outputs and goal answers or outputs. Initial processes to be improved may be created by a programmer or user or may be generated according to a given machine-learning algorithm using data initially available. Inputs and goal outputs may be provided in two data sets from which the machine learning algorithm may derive the above-described calculations; for instance a first set of inputs and corresponding goal outputs may be provided and used to create a mathematical relationship between inputs and outputs that forms a basis of an initial or intermediate process, and which may be tested against further provided inputs and goal outputs. Data sets representing inputs and corresponding goal outputs may be continuously updated with additional data; machine-learning process may continue to learn from additional data produced when machine learning process analyzes outputs of "live" processes produced by machine-learning processes. As a non-limiting example, an unsupervised machine-learning algorithm may be performed on training sets describing co-occurrences of any or all parameters in time; unsupervised machine-learning algorithm may calculate relationships between parameters and such co-occurrences. This may produce an ability to predict a likely change in a physiological parameter as a function of detected changes in one or more environmental parameters; thus, a physiological alarm condition may be detected when a set of alarm parameters are trending in a way associated with decreases in blood oxygen, causing a blood oxygen warning to be generated before any decrease in blood oxygen is detected. With continued reference to FIGS. 1-5, a supervised machine learning algorithm may be used to determine an association between one or more detected parameters and one or more physiological alarm conditions or other outcomes or situations of interest or concern. For instance, a supervised machine-learning algorithm may be used to determine a relationship between one or more sets of parameters, such as physiological parameters, environmental parameters, and/or user-entered information, and one or more physiological alarm conditions. To illustrate, a mathematical relationship between a set of physiological and environmental parameters as described above and a loss of consciousness, or near loss of consciousness, by user, may be detected by a supervised machine-learning process; such a process may include a linear regression process, for instance, where a linear combination of parameters may is assumed to be associated with a physiological alarm condition, and collected parameter data and associated data describing the physiological alarm condition are evaluated to determine the linear combination by minimizing an error function relating outcomes of the linear combination and the real-world data. Polynomial regression may alternatively assume one or more polynomial functions of parameters and perform a similar minimization process. Alternatively or additionally neural net-based algorithms or the like may be used to determine the relationship.

Still viewing FIGS. 1-5, each of the above processes for aggregation and/or machine learning may further be compared to test data, such as data gathered concerning user physiological parameters, performance, and/or function, in one or more testing facilities or protocols; such facilities or protocols may include, for instance, centrifuge testing of a user's response to acceleration and/or G forces, tests administered to monitor one or more physiological parameters and/or user function or performance under various adverse conditions such as sleep deprivation, boredom, and the like, or any other tests administered to determine the effect of various conditions on user. Such test data may be collected using device 100, or alternatively may be collected using one or more other devices, medical facilities, and the like. Any aggregation and/or machine learning as described above may be applied to test data, independently or combined with other data gathered as described above; for instance, in an embodiment, test data may be combined with typical user data to achieve a first baseline, which may be compared to further data gathered as described above to modify the baseline and generate a second baseline using any suitable aggregation or machine-learning methodology. Collected and/or aggregated data may be provided to users, such as supervisors or commanders, who may use collected and/or aggregated data to monitor state of health of individual users or groups of users. In an embodiment, device 100 may store data collected during a period of activity, such as a flight where device 100 is used with a pilot and may provide such data to another device upon completion of the period of activity. For instance, device 100 may download stored data into a file for storage and tracking; data file may be analyzed using an indigenously designed application to determine areas of further study, allowing a detailed look at portions of ground operations or flight in which physiological responses can be compared to known conditions. File and/or collected data may be transferred to a remote computing device via network, wired, or wireless communication; for instance, and without limitation, device 100 may be connected to or placed in communication with remote device after each flight or other period of activity. Where device 100 is incorporated in an element of headgear such as a helmet, headset, and/or mask, such element of headgear may be connected via wired, wireless, and/or network connection to remote device.

With continued reference to FIGS. 1-5, in an illustrative example, detection of a physiological alarm condition may include determination, by the training and feedback processor 120, that the user is losing consciousness. Alternatively or additionally, detection may include determination that user is about to lose consciousness. This may be achieved by comparing one or more physiological parameters and/or environmental parameters to a relationship, threshold, or baseline, which may be any relationship, threshold, or baseline as described above; for instance and without limitation, where blood oxygen level drops below a threshold percentage of a baseline level, below an absolute threshold amount, below a certain number of standard deviations, or the like, training and feedback processor 120 may determine that user is about to lose consciousness or is losing consciousness, and issue an alarm. Alternatively or additionally, aggregation as described above may determine that imminent loss of consciousness is predicted by a particular set of values for one or more parameters as described above, training and feedback processor 120 may detect a physiological alarm condition by detecting the particular set of values, indicating that user is about to lose consciousness. In an embodiment, determination of user state and/or physiological alarm condition may filter out anomalous or transient readings, or readings altered by motion of one or more elements of user's body or environment; for instance, determination may include determination of a particular parameter value for longer than a predetermined amount of time.

As another example, and still viewing FIGS. 1-5, detection of the physiological alarm condition further comprises determination that the user is falling asleep; this may occur, for instance, where a neural activity sensor detects that a user is entering into an early stage of sleep, or "dozing off," for instance by detection of a change in brainwaves. In an embodiment, training and feedback processor 120 may generate an alarm where alpha wave activity drops by a threshold percentage, by a threshold amount, or the like; alternatively or additionally, one or more sets of brainwave patterns determined by training and feedback processor 120 to be associated with user falling asleep, for instance by aggregation or machine-learning methods as described above, may be detected by training and feedback processor 120 via at least a neural activity sensor, triggering an alarm. This may, as a non-limiting example, aid in preventing a commercial pilot who is not actively operating flight controls from partially or wholly falling asleep, which is a particular concern on long flights.

With continued reference to FIGS. 1-5, detection of a physiological alarm condition may further include detection of at least an environmental parameter, and detection of physiological alarm condition as a function of the at least an environmental parameter. For instance, aggregation and/or machine learning processes as described above may determine that a reduction in cranial blood pressure coupled with an increase in acceleration indicates a probable loss of consciousness in a user; an alarm may therefore be triggered by detection, by training and feedback processor 120, of that combination of decreased cranial blood pressure and increased acceleration.

Still viewing FIGS. 1-5, training and feedback processor 120 may incorporate or be in communication with at least a user-signaling device 128. In an embodiment, at least a user-signaling device 128 may be incorporated in device 100; for instance, at least a user-signaling device 128 may be attached to or incorporated in housing 104. Where at least a user-signaling device 128 contacts an exterior body surface of user, housing 104 may act to place at least a user-signaling device 128 in contact exterior body surface of user. Alternatively or additionally, device 100 may communicate with a user-signaling device 128 that is not incorporated in device 100, such as a display, headset, or other device provided by a third party or the like, which may be in communication with training and feedback processor 120. User-signaling device 128 may be or incorporate a device for communication with an additional user-signaling device such as a vehicle display and/or helmet avionics; for instance, user-signaling device 128 may include a wireless transmitter or transponder in communication with such additional devices. In an embodiment, and without limitation, user-signaling device 128 may be configured to indicate the degree of pilot hypoxemia to at least a user, as described in further detail below.

Continuing to refer to FIGS. 1-5, at least a user-signaling device 128 may include any device capable of transmitting an audible, tactile or visual signal to a user when triggered to do so by training and feedback processor 120. In an embodiment, and as a non-limiting example, at least a user-signaling device 128 may include a bone-conducting transducer in vibrational contact with a bone beneath the exterior body surface. A bone-conducting transducer, as used herein, is a device or component that converts an electric signal to a vibrational signal that travels through bone placed in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing 104 in a position placing it in contact with a user's bone; for instance, where housing 104 includes or is incorporated in an ear cup, housing 104 may place bone-conducting transducer in contact with user's skull just behind the ear, over the sternocleidomastoid muscle. Likewise, where housing 104 includes a headset, mask, or helmet, housing 104 may place bone-conducting transducer in contact with a portion of user's skull that is adjacent to or covered by headset, mask, or helmet.

Still referring to FIGS. 1-5, at least a user-signaling device 128 may further include an audio output device. Audio output device may include any device that converts an electrical signal into an audible signal, including without limitation speakers, headsets, headphones, or the like. As a non-limiting example, audio output device may include a headset speaker of a headset incorporating or connected to device 100, a speaker in a vehicle user is traveling in, or the like. At least a user-signaling device 128 may include a light output device, which may be any device that converts an electrical signal into visible light; light output device may include one or more light source 604s such as LEDs, as well as a display, which may be any display as described below in reference to FIG. 11. At least a user-signaling device 128 may include a vehicular display; at least a vehicular display may be any display or combination of displays presenting information to a user of a vehicle user is operating. For instance, at least a vehicular display may include any combination of audio output devices, light output devices, display screens, and the like in an aircraft flight console, a car dashboard, a boat dashboard or console, or the like; training and feedback processor 120 may be in communication with vehicular display using any form of communicative coupling described above, including without limitation wired or wireless connection. At least a user-signaling device 128 may include a helmet display; helmet display may include any visual, audio, or tactile display incorporated in any kind of helmet or headgear, which may be in communication with training and feedback processor 120 according to any form of communicative coupling as described above.

Still viewing FIGS. 1-5, user-signaling device 128 and/or training and feedback processor 120 may be programmed to produce a variety of indications, which may correspond to various physiological alarm conditions and/or contexts. Possible indications may be, but are not limited to: imminent unconsciousness, substandard oxygenation, erratic pulse, optimum oxygenation, and/or any other suitable indication, while maintaining the spirit of the present invention. Each such indication may have a distinct pattern of audible, visual, and/or textual indications; each indication may include, for instance, an audible or textual warning or description of a physiological alarm condition. Any of the above user-signaling devices 128 and/or signals may be used singly or in combination; for instance, a signal to user may include an audio signal produced using a bone-conducting transducer, a verbal warning message output by an audio output device, and a visual display of an image or text indicating the physiological alarm condition. Persons skilled in the art, upon reviewing the entirety of this disclosure, will be aware of various combinations of signaling means and/or processes that may be employed to convey a signal to user. In an embodiment, in addition to transmitting an alarm to user-signaling device 128, alert circuit may transmit a signal to one or more automated vehicular controls or other systems to alleviate one or more environmental parameters contributing to physiological alarm condition. For instance, and without limitation, an automated aircraft control may receive an indication of hypoxia while a motion sensor indicates high acceleration; aircraft control may reduce acceleration to alleviate the hypoxia. Persons skilled in the art, upon reviewing the entirety of this disclosure, may be aware of various additional ways in which automated systems may act to alleviate a physiological alarm condition as described herein.

Figure 8:
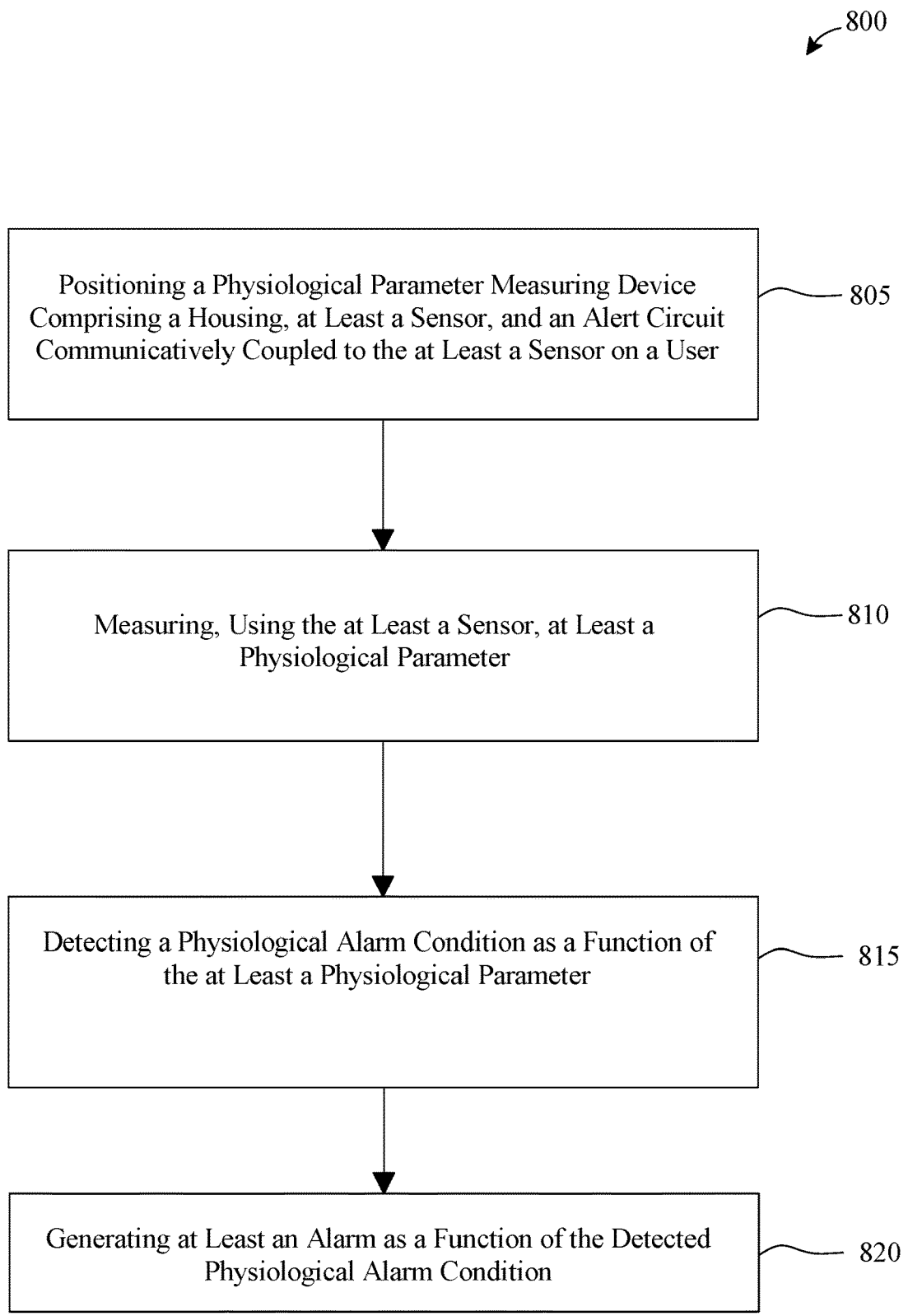
FIG. 8 shows a flowchart of a method of using the human performance oxygen sensor according to an embodiment of the present invention.

Referring now to FIG. 8, an exemplary embodiment of a method 800 of measuring physiological parameters 100 is illustratively depicted. At step 805, a physiological parameter measuring device comprising a housing 104, at least a physiological sensor 116, and a training and feedback processor 120 in communication with the at least a physiological sensor 116 is positioned on a user. This may be performed, for instance, as described above in reference to FIGS. 1-5. Positioning may include mounting housing 104 on an exterior body surface of the user. Positioning may include placing at least a physiological sensor 116 in contact with exterior body surface. As a non-limiting example, at least a physiological sensor 116 may rest behind the ear on the neck of the user, over the sternocleidomastoid muscle. In an embodiment, mounting device 100 to user includes mount a plurality of devices to user. For instance, and without limitation, where device 100 includes an ear cup as described above, user may be outfitted with two such devices (one in each ear cup); low-confidence data points may be validated by the second sensor, essentially "filling-in" the holes in data coverage.

At step 810, with continued reference to FIG. 8, training and feedback processor 120 measures at least a physiological parameter using at least a physiological sensor 116. In an embodiment, this may be performed as described above in reference to FIGS. 1-5. For instance, where sensor includes at least a NIRS 600 sensor, sensor may measure one or more signals from the user pertaining to the oxygenation of the user. The signals may include, but are not limited to, pulse oximetry, pulse, temperature, and/or any other relevant measurement. NIRS 600 sensor may emit near-infrared (red) light into soft tissue and measure how much of the near-infrared light is absorbed by said tissue and how much is reflected. According to an embodiment, the sensing components of the NIRS 600 sensor may act essentially as specialized photoresistors. Their resistivity may change as a function of the intensity of light reflected from the tissue. Since well-oxygenated blood (defined as oxygen-bound hemoglobin) absorbs more red light than poorly oxygenated blood, a correlation between the resistivity of the sensor and the blood oxygenation may be ascertained as a function of the resistivity.

Still viewing FIG. 8, at step 815, a physiological alarm condition is detected by training and feedback processor 120 as a function of the at least a physiological parameter. This may be implemented, for instance, as described above in reference to FIGS. 1-5. For example, and without limitation, training and feedback processor 120 may predict whether a user is going to experience an impending lack of consciousness. According to an embodiment, training and feedback processor 120 may constantly monitor blood oxygenation by virtue of aNIRS sensor. According to an embodiment, when oxygenation drops by a predefined percentage, the training and feedback processor 120 may predict that the user is going to experience an impending lack of consciousness. Any other combination of physiological and/or environmental parameters may be used to detect physiological alarm condition, as described above in reference to FIGS. 1-5.

With continued reference to FIG. 8, at step 820, training and feedback processor 120 generates at least an alarm as a function of the detected physiological alarm condition. This may be performed as described above in reference to FIGS. 1-5. Training and feedback processor 120 may signal user as a function of detected physiological alarm condition; this may be implemented as described above in reference to FIGS. 1-5. For instance, and without limitation, where training and feedback processor 120 predicts that the user is going to experience an impending lack of consciousness, the training and feedback processor 120 may sends a signal to bone conduction transducer, generating a user signal. Similarly, and as described above, training and feedback processor 120 may further send a signal to a third-party device, either wirelessly or through a wired connection, alerting a third party of any relevant predictions made by the training and feedback processor 120 while the device for measuring physiological parameters 100 is being used.

Device for measuring physiological parameters 100 may be used is various fields, according to various embodiments of the present invention. According to an embodiment, the device for measuring physiological parameters 100 may be used in conjunction with military aviation. For example, the human performance oxygen sensor may be used for military aviation uses that rely on stored oxygen, e.g., for use in fighter jets and high-altitude parachuting. During operation of fighter jets and while performing high altitude parachuting, there is a risk of hypoxia and the inherent need to wear a helmet. The device for measuring physiological parameters 100 may be incorporated into such helmets, thus measuring the wearer's vital oxygenation signals while the wearer is wearing the helmet.

According to various embodiments, device for measuring physiological parameters 100 may be used in conjunction with commercial aviation headsets, firefighting uses, and/or in any other suitable field where the measurement of human oxygenation is relevant or necessary for the safety of individuals or for any other relevant reason. According to various embodiments, iterative additional developments of the product include incorporation of a carbon dioxide sensor, reduction in size/weight, removal of the battery to utilize host system available power from the aircraft or vehicle, and/or the inclusion or exclusion of various other suitable components while maintaining the spirit of the present principles. In testing performed using a reduced oxygen breathing device (ROBD) to simulate atmospheric conditions at various altitudes, in which device 100 was compared to a conventional finger-mounted oxygen sensor, it was found that embodiments of device 100 were able to detect decreased blood oxygen levels up to 15 seconds earlier than previously available systems, resulting in a substantially improved opportunity for users to correct conditions leading to hypoxia; this in turn allowed users to avert symptoms of hypoxia in some cases, and generally to reduce the length and severity of symptoms, both of which are crucial for improving outcomes during flight. Alarms were triggered by device 100 just as users were reporting initial sensation of symptoms. Subsequent testing on flight sorties confirmed high degrees of reliability in detection of physiological alarm conditions.

According to various embodiments, device 100 may further include incorporation of a pulse oximetry sensor and a carbon dioxide sensor to incorporate the existing product into a fire helmet. The and signaling may be transmitted to an existing or newly developed two-way radio system in order to allow a fire chief to receive real-time data on all the members of his firefighting force. By transmitting and receiving this data, the fire chief is able to receive real time location and performance data of every single member of his time, optimizing the team's performance.

Embodiments of the above-described devices and methods may provide a system that produces real-time, accurate physiological data analysis. In an embodiment, sensing hematological parameters from a branch of a user's carotid artery enables more rapid and accurate detection of physiological conditions, such as hypoxemia; this may permit a user to operate under difficult conditions for longer, knowing that a timely and accurate warning system is in place to indicate when conditions should be modified. Machine learning and data analysis may continuously improve formulas for detection of physiological alarm conditions, yielding greater accuracy in predicting imminent incapacitation before it has progressed to the point where a user is unable to act to prevent it.

Figure 9:
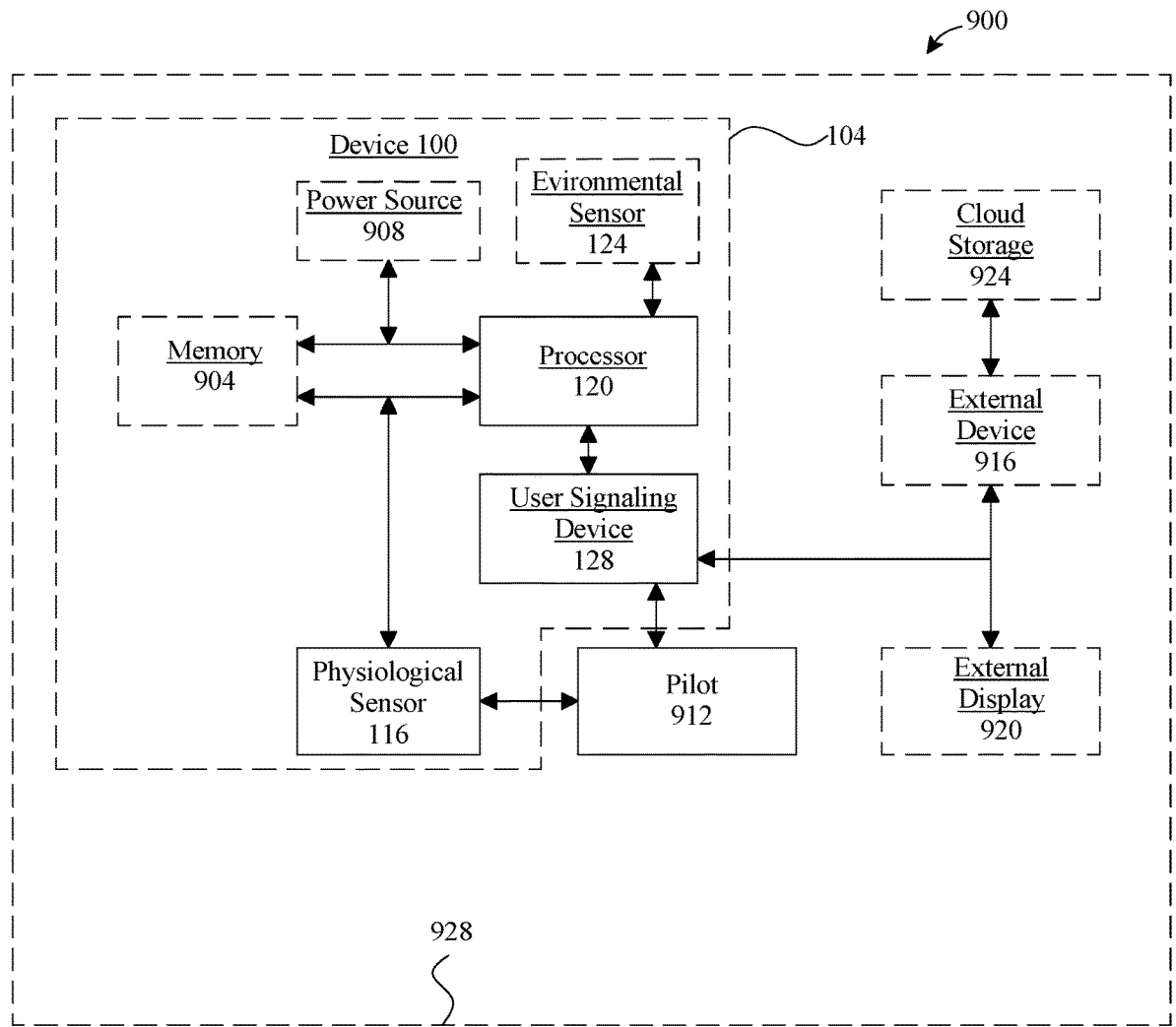
FIG. 9 illustrates a block diagram of an embodiment of a system incorporating a device according to an embodiment.

Referring now to FIG. 9, an embodiment of device 100 in use as a device for training pilots using physiological sensor feedback for flight circumstances that cause hypoxia is illustrated. Device 100 may be incorporated in a system 900 for training pilots using physiological sensor feedback. Device 100 may be any device as disclosed above; device includes a training and feedback processor 120, which may include any training and feedback processor 120 as described above in reference to FIGS. 1-8. Training and feedback processor 120 is in communication with at least a physiological sensor 116, which may include any physiological sensor as described above in reference to FIGS. 1-8. Device 100 may include and/or communicate with a user signaling device 128, which may include any user signaling device 128 as described above in reference to FIGS. 1-8. Device may include a memory 904, which may be a solid-state memory or the like; memory 904 may be used to record data during test periods, sorties, simulations, and the like, for instance as described above in reference to FIGS. 1-8. Device 100 may include a power source 908, which may include without limitation a local power storage device such as a battery or fuel cell.

Continuing to refer to FIG. 9, and as further described above in reference to FIGS. 1-8, device may include a housing 104. Housing may be configured to be mounted to a pilot 912 or other user to be trained or regarding whom data is to be gathered; it should be understood that pilot 912 is illustrated here only to indicate a manner in which device 100 interacts with a user and does not imply that pilot 912 is a part of system 900 and/or device 100. Housing may be mounted to pilot 912 or other user as described above in reference to FIGS. 1-8. For instance, and without limitation, housing may be mounted so as to place at least a physiological sensor 116 in contact with a locus on pilot 912 and/or other user as described above in reference to FIGS. 1-8.

Still viewing FIG. 9, device 100 may communicate at times with an external device 916; communication may be continuous or episodic. For instance, and as described above in reference to FIGS. 1-8, device 100 may communicate with external device 916 at the end of a sortie, simulation, or testing period to provide data collected during the sortie, simulation, or testing period; alternatively or additionally, device 100 may communicate continuously with external device 916 during at least a portion of sortie, simulation, and/or testing period, for instance to provide information to a person coordinating the sortie, simulation, or testing period, such as a commanding officer or the like. External device 916 may alternatively or additionally include a device incorporated in a simulation environment, vehicle, aircraft, or the like. System 900 may include or communicate with an external display 920. For instance, and without limitation external device 916 may provide information to an external display 920 including a monitor, audio communication device, or the like to a commanding officer, person recording a simulation, or the like. External display 920 may include a vehicular display as described above; vehicular display may receive information from user signaling device 128 and/or other components of device 100 to provide information to user and/or pilot 912. Data may be relayed from external device 916 to further memory devices and/or systems such as without limitation cloud storage 924; data may be analyzed in combination with additional data captured from pilot 912 or other user, for instance during other sorties, simulations, or test periods, from additional users, or the like, and may be analyzed as described above to detect relationships between data detected by physiological sensors and/or environmental sensors as described above. Any relationship between any element of data captured by one or more physiological sensors, any element of data captured by one or more environmental sensors, and/or any element of data concerning a flight circumstance as described in further detail below, may be analyzed, calculated, and/or determined using machine learning and/or data analysis as described above.

Still referring to FIG. 9, device 100 may be installed in, and/or system 900 may include, a flight condition generating device 928. Flight condition generating device 928 as used herein includes any device that alters environmental parameters in a manner consistent with alternations that may be encountered during circumstances for which a user may be trained, including conditions likely to occur during a flight. Such conditions may include variations in atmospheric and/or respirator oxygen, variations in temperature, variations in barometric pressure, variations in acceleration and/or or G forces, or the like. Flight condition generating device 928 may include a chamber and/or device in which oxygen levels and/or barometric pressure may be adjusted such as without limitation a Reduced Oxygen Breathing Device (ROBD), a centrifuge or other device that varies G forces experienced by a user, a flight simulator, and/or an aircraft, including an aircraft the user and/or pilot 912 is being trained to use.

Figure 10:
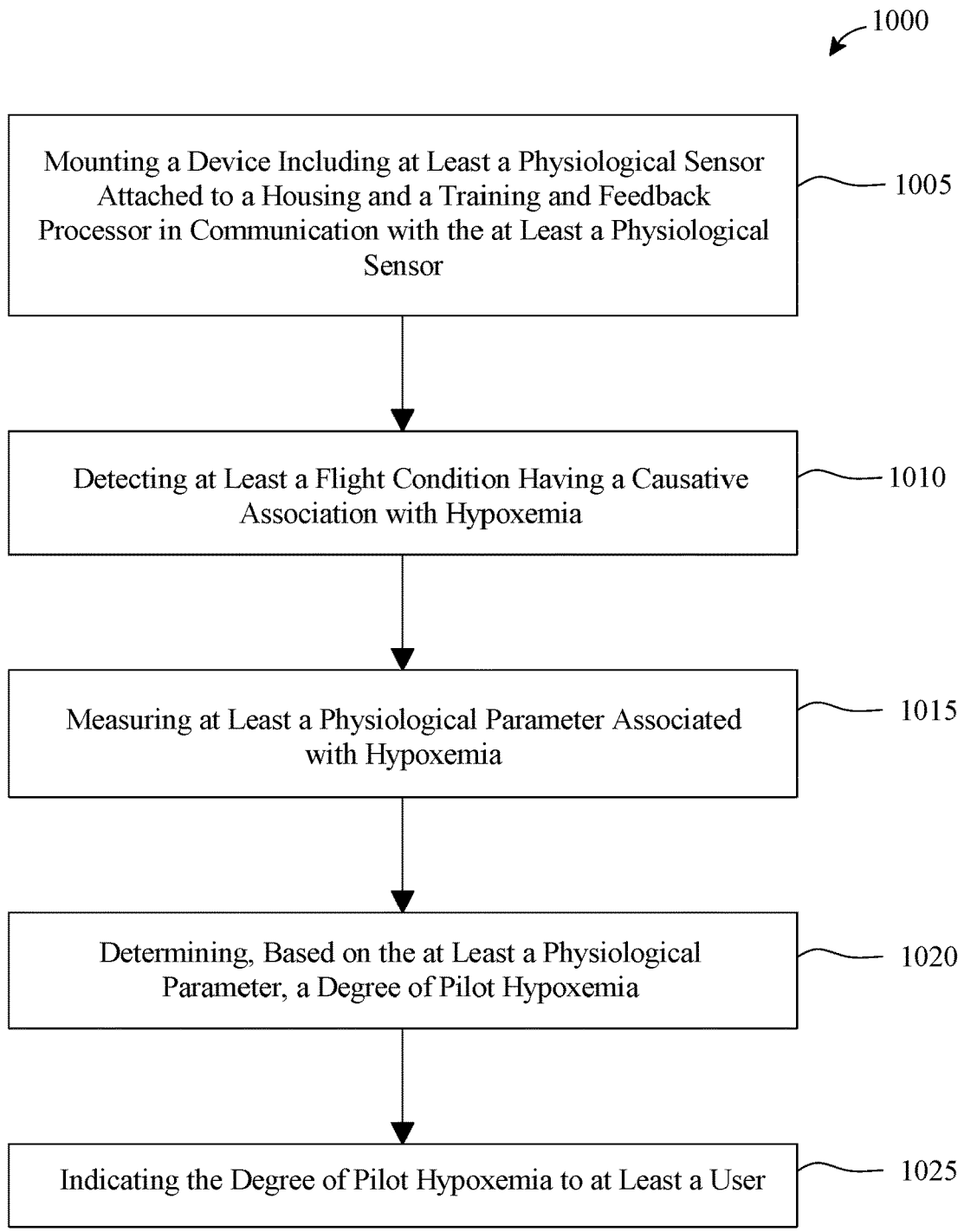
FIG. 10 is a flow diagram of an exemplary embodiment of a method of training pilots using physiological sensor feedback.

Referring now to FIG. 10, an exemplary embodiment of a method 1000 of training pilots using physiological sensor feedback for flight circumstances that cause hypoxemia is illustrated. At step 1005, a device 100 for physiological sensor feedback is mounted to a user; user may be a pilot 912. Device 100 includes a housing 104 at least a physiological sensor attached to the housing and configured to detect at least a physiological parameter associated with hypoxemia 116 and a training and feedback processor 120 in communication with the at least a physiological sensor 116, as described above in reference to FIGS. 1-8. Mounting device 100 to user may be performed according to any process or process steps as described above in reference to FIGS. 1-8.

At step 1010, and still referring to FIG. 10, training and feedback processor 120 detects at least a flight condition having a causative association with hypoxemia. A flight condition, as used herein, is any set of circumstances in an aircraft, flight simulator, or other flight condition generating device 928; at least a flight condition may include any state of environment or modification to environment within a flight condition generating device 928 that flight condition generating device 928 is commanded by a person or system to perform, including a change in air pressure, oxygen content, acceleration, direction, rotational or angular velocity, barometric pressure, variations in temperature, or the like. At least a flight condition may include any condition detectable using at least an environmental sensor 124. At least a flight condition having a causative association with hypoxemia may include any circumstance in a flight and/or flight simulation tending to cause either generalized or cranial/cerebral hypoxemia, including without limitation high G-forces imposed by acceleration of an aircraft, motion of a centrifuge, or the like, low atmospheric and/or respirator oxygen contents, low barometric pressure, and the like. Data analysis and/or machine learning as described above may be used to detect relationships between flight conditions and hypoxemia.

Still referring to FIG. 10, training and training and feedback processor 120 may detect the at least a flight condition by receiving data indicating a flight condition that a flight condition generating device 928 is generating from the flight condition generating device 928. For instance, a device, such as an ROBD or the like, that adjusts atmospheric oxygen levels and/or barometric pressure experienced by a pilot 912 may receive and/or automatically generate a command to adjust oxygen level and/or barometric pressure; the command may be transmitted and/or otherwise provided to training and training and feedback processor 120 as a flight condition. As a further example, where flight condition generating device 928 is a device that varies G forces on a user, such as a centrifuge, flight condition generating device 928 may receive or automatically generate a command to increase and/or decrease G forces on user, such as a command to increase and/or decrease angular velocity of a centrifuge; this command may be transmitted or otherwise provided to training and feedback processor 120 as a flight condition. Where flight condition generating device 928, one or more commands from pilot 912, autopilot guidance computer or instrumentation, or the like may be provided to training and feedback processor 120; for instance, pilot manual controls in a fly-by-wire or partial fly-by-wire aircraft may take the form of electronic signals, which may also be transmitted and/or provided to training and feedback processor 120. Flight plan or precalculated trajectory data may be provided to training and feedback processor 120 as part of data describing at least a flight condition; for instance, a fly-by-wire system may be programmed to respond to a particular pilot and/or autopilot command by causing an aircraft to traverse a certain trajectory at a certain velocity or with a certain acceleration.

Continuing to refer to FIG. 10, training and training and feedback processor 120 may detect at least a flight condition using at least an environmental sensor 124. Detection may be performed according to any process described above for detection of environmental parameters using at least an environmental sensor 124 that is part of device 100 or external to device 100 and in communication with device 100. For instance, and without limitation, an oxygen sensor may detect an oxygen level, a temperature sensor may detect a temperature level, a barometric pressure sensor may detect a barometric pressure level, and a motion sensor may detect G forces, acceleration.

Still referring to FIG. 10, detection of at least a flight condition may include a combination of receiving data from a flight condition generating device 928 and detection using at least an environmental sensor 124. For instance pilot 912 and/or autopilot may direct an aircraft to climb to a certain altitude at a certain velocity, which may be provided to training and feedback processor 120, while motion, oxygen, and/or pressure sensors may detect actual conditions, which may vary from expected conditions.

At step 1015, training and training and feedback processor 120 measures at least a physiological parameter associated with hypoxemia using at least a physiological sensor 116. Measuring may include measuring at least a hematological parameter. At least a hematological parameter may include a heart rate. At least a hematological parameter may include a blood oxygen level. At least a physiological parameter may include two or more hematological parameters; for instance, and as described in further detail above, at least a physiological parameter may include a combination of heart rate and blood oxygen saturation. For instance, changes to heart rate and changes in blood oxygen saturation may be detected concurrently or at temporally proximate points, as described in further detail above in reference to FIGS. 1-8.

At step 1020, and still referring to FIG. 10, training and feedback processor 120 determines a degree of pilot hypoxemia based on the physiological parameter. For instance, where measuring includes measuring at least a hematological parameter determining may include determining the at least a hematological parameter is associated with the level of hypoxemia; this may be accomplished, without limitation, as described above. For instance, where measuring includes measuring a blood oxygen level, determining may include determining that the detected blood oxygen level is associated with the level of hypoxemia. This may be performed according to thresholds indicating levels of probable degrees of impairment associated with various percentages of blood oxygen saturation as described above; thresholds may include default thresholds set by factory or according to typical users, and/or thresholds set according to user values, for instance using changes to default thresholds as directed by data collected concerning user. As a further non-limiting example, where the at least a hematological parameter includes a heart rate, determining may include determining that the detected heart rate is associated with a level of hypoxemia; for instance and without limitation, an increase in heart rate, a change in blood pressure, or the like may indicate a likely movement from one threshold to another regarding blood oxygen saturation levels. Where measuring includes measuring a heart rate and a blood oxygen level, which may be a blood oxygen saturation level, determination may include determining that a combination of blood oxygen level and heart rate is associated with the level of hypoxemia; this may be performed as described above in reference to FIGS. 1-8.

Still referring to FIG. 10, degree of hypoxemia may include a non-impairing degree of hypoxemia as described above; for instance, degree of hypoxemia may meet a threshold for a "possible problem," which may also serve as an indication that blood oxygen condition of pilot 912 may be likely to deteriorate further. Degree of hypoxemia may include an impairing degree of hypoxemia; an impairing degree of hypoxemia may, for instance, relate to a second threshold as described above, for "performance degraded." Degree of hypoxemia may include a degree of hypoxemia associated with an imminent loss of consciousness. Degree of hypoxemia may be determined by relationships between detected factors and/or physiological parameters. For instance, and without limitation, a decrease in blood oxygen saturation of 5% by itself may not suffice to trip a threshold based on blood oxygen saturation alone, but a concomitant increase in heart rate or decrease in blood pressure may cause training and feedback processor 120 to determine that pilot 912 has arrived at a higher or more severe degree of hypoxemia. As a further non-limiting example, one or more factors detected using at least a physiological sensor 116 and/or at least an environmental sensor 124 may cause training and feedback processor 120 to treat a given hematological or other parameter as indicating a more or less severe degree of hypoxemia; such factors may include, without limitation, (1) detection of a degree of hydration of the pilot 912, where a lower degree of hydration may be associated with more acute hypoxemia for a given blood oxygen saturation level and/or heart rate; (2) a degree of pilot fatigue as determined, for instance, by brain wave activity, history or length of recent activity, or the like, and where a higher degree of fatigue or greater amount of recent flight activity may be associated with a more severe level of hypoxemia for a given blood oxygen saturation percentage and/or heart rate; (3) detected changes in neural oscillations, where, for instance, change indicating a tendency toward drowsiness, and or indication of entry into early stages of sleep or the like, where greater drowsiness and/or incipient hypnagogic states may indicate a higher degree of hypoxemia for a given blood oxygen saturation level and/or heart rate; (4) detected changes in ketone or VOC emission by user, where greater ketone and/or VOC emission indicates a higher degree of fatigue, which may be used as described above, and/or a more severe degree of hypoxemia for a given blood oxygen saturation level and/or heart rate; and/or (5) temperature, where a temperature significantly higher or lower than room temperature may be associated with a more severe degree of hypoxemia for a given blood oxygen saturation percentage and/or heart rate. Each such factor, or any combination thereof, may also be associated by training and feedback processor 120 with a greater or lesser projected rate of degradation of pilot's degree of hypoxemia; for instance, a more fatigued pilot, or less hydrated pilot, may be more likely to descend from a current level of hypoxemia to a worse level than a well-rested or adequately hydrated pilot. A cumulative fatigue model may be generated or applied to determine a degree to which pilot fatigue affects either a current level of hypoxemia or a likely future rate of degradation. Degree of hypoxemia may include a degree of generalized or systemic hypoxemia, and/or a degree of cerebral and/or cranial hypoxemia.

At step 1025, and continuing to refer to FIG. 10, method 1000 includes indicating using a user-signaling device 128, degree of pilot hypoxemia to at least a user. At least a user may include pilot 912; for instance, and as described in further detail above, an alarm may be transmitted to pilot via user-signaling device 128, including without limitation through a bone-conducting transducer or other alarm signal, a vehicular display, or the like. At least a use may include a person who is not pilot 912, such as a commanding officer, a person administering a test or training session, or the like. Indication may include an instruction or recommendation to act to alleviate conditions that may be causing a degree of hypoxemia; for instance, instruction or recommendation may instruct or recommend a modification to motion being undertaken by flight condition generating device 928 to decrease G forces on the pilot 912, a recommendation to increase oxygen levels and/or air pressure in an ROBD or similar device, a recommendation to decrease altitude of an aircraft, or the like. In an embodiment, training and feedback processor 120 may transmit an instruction to a flight condition generating device 928 to change the flight condition; flight condition generating device 928 may, for instance, automatically reduce G forces or increase air pressure or oxygen levels With continued reference to FIG. 10, training and feedback processor 120 generates at least a pilot-specific flight guideline using the at least a flight condition and the level of hypoxemia. Generation of at least a pilot-specific flight guideline may include determining an association between at least a physiological condition, at least a flight condition, and/or other information concerning pilot and/or other user. At least a pilot-specific flight guideline may be based on baseline data regarding pilot 912, on one or more training or mission goals, or both. For instance, a goal of a training session may be for a pilot 912 to operate under light (e.g., relating to a first threshold level as described above) to moderate (e.g., relating to a second threshold level as described above) hypoxemia, for a certain period of time intended, for instance, to indicate circumstances under which a mission-critical or otherwise important maneuver or act must be performed at high altitudes, high speeds, or other circumstances likely to induce at least a degree of hypoxemia; length of period and/or degree of hypoxemia experienced may be set according to pilot's record of past performance, baselines recorded regarding that pilot's performance under light to moderate hypoxemia and/or that pilot's tendency to degrade to higher degrees of hypoxemia under some circumstances, or the like. Another goal may, for instance be to have pilot 912 undergo a particular environmental condition, such as atmospheric oxygen below a set level and/or a series of high-G maneuvers and/or periods, and to attempt and/or practice strategies for avoiding incapacitation. A second instruction may issue, as well; for instance, if pilot 912 is degrading more than expected, a training session may be modified to be less severe or aborted. At least a pilot-specific flight guideline may be provided to at least a user and/or a flight condition generation device 928 as an instruction, as described above. As noted above, any data regarding past pilot performance, baselines, and the like, together with correlated physiological parameters, environmental parameters, and/or flight conditions as described above may be analyzed using data analysis and/or machine learning as described above, to derive mathematical relationships between various factors; such relationships can be used to set thresholds, for instance as described above, and to plan pilot training and/or missions to remain within certain threshold ranges, to increase pilot resistance to hypoxemia and extend such threshold ranges, or the like. In an embodiment, both device 100 and pilot may learn in each mission and/or training session to work more effectively within the physiological limits of the pilot, enabling a greater range of actions to be performed to a higher degree of safety. Methods as described herein and/or device 100 may enable training profiles to identify potential shortfalls and/or difficulties, for instance by modifying training profiles and/or plans to avoid detected episodes of hypoxemia, either for particular pilots 912, for particular cohorts or demographic sets of pilots, or for pilots in general.

Although methods, devices, and systems have been described above for training pilots for circumstances that may involve hypoxemia, embodiments described above may similarly be used to train other persons for other situations likely to involve and/or induce hypoxemia; flight condition may, in other words, be replaced by a mission condition and/or other condition specific to a particular situation. Such alternatives may include training for astronauts/cosmonauts, firefighters, divers, mountaineers, athletes, or the like.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
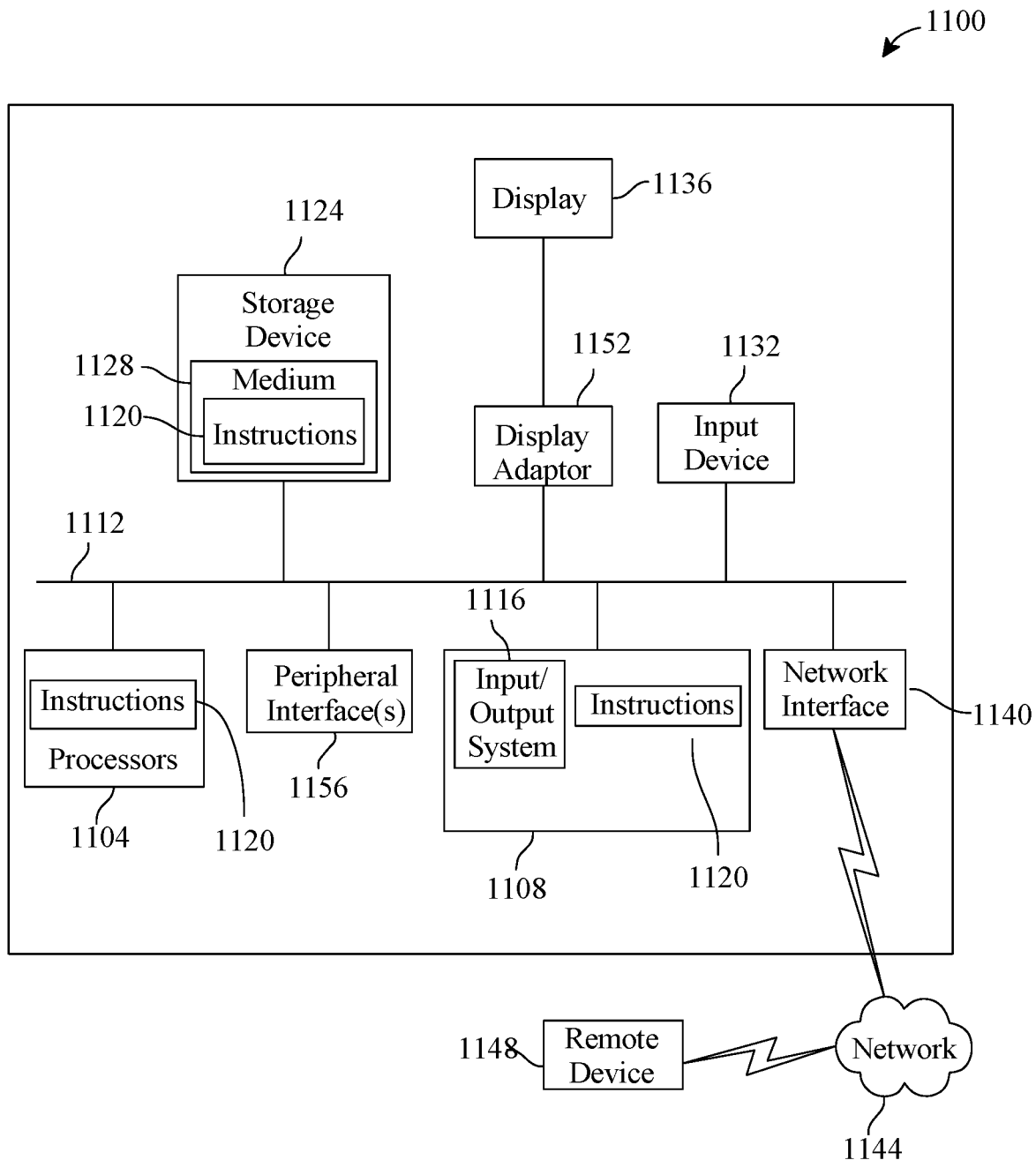
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system, such as the device 100 disclosed above, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, devices and/or software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A device for training pilots using physiological sensor feedback for flight circumstances that cause hypoxemia, the device comprising:
    a housing configured to be mounted to an exterior body surface of a user;
    at least a physiological sensor attached to the housing and configured to detect at least a physiological parameter associated with hypoxemia; and
    a training and feedback processor in communication with the at least a physiological sensor, the training and feedback processor designed and configured to:
        detect at least a flight condition having a causative association with hypoxemia;
        measure, using the at least a physiological sensor, at least a physiological parameter associated with hypoxemia;
        determine, by the training and feedback processor, and based on the at least a physiological parameter, a degree of pilot hypoxemia;
        determine a training goal associated with hypoxemia; and
        generate a pilot-specific flight guideline based upon the degree of pilot hypoxemia and the training goal associated with hypoxemia; and
    a user signaling device in communication with the training and feedback processor, the user signaling device configured to indicate the degree of pilot hypoxemia to at least a user.

2. The device of claim 1, wherein the at least a physiological sensor further comprises a heart-rate sensor.

3. The device of claim 1, wherein the at least a physiological sensor further comprises a blood oxygen sensor.

4. The device of claim 1, wherein the at least a physiological sensor is configured to detect at least a hematological parameter of at least a branch of a carotid artery.

5. The device of claim 4, wherein the housing is further configured to place the at least a physiological sensor in proximity to the at least a branch of the carotid artery.

6. The device of claim 1 further comprising at least an environmental sensor.

7. The device of claim 6, wherein the at least an environmental sensor includes at least a motion sensor.

8. The device of claim 6, wherein the at least an environmental sensor includes at least atmospheric oxygen sensor.

9. The device of claim 6, wherein the at least an environmental sensor includes at least a barometric sensor.

10. A method of training pilots using physiological sensor feedback for flight circumstances that cause hypoxemia, the method comprising:
    mounting a device for physiological sensor feedback to a user, wherein the device further comprises a housing, at least a physiological sensor attached to the housing and configured to detect at least a physiological parameter associated with hypoxemia, and a training and feedback processor in communication with the at least a physiological sensor;
    detecting, by the training and feedback processor, at least a flight condition having a causative association with hypoxemia;
    measuring, using the at least a physiological sensor at least a physiological parameter associated with hypoxemia;
    determining, by the training and feedback processor, and based on the at least a physiological parameter, a degree of pilot hypoxemia;
    determining, by the training and feedback processor, a training goal associated with hypoxemia;
    generating a pilot-specific flight guideline based upon the degree of pilot hypoxemia and the training goal associated with hypoxemia; and
    indicating, using a user signaling device, the degree of pilot hypoxemia to at least a user.

11. The method of claim 10, wherein detection of the at least a flight condition further comprises receiving, from a flight condition generating device, data indicating a flight condition.

12. The method of claim 10, wherein detection includes detection of the at least a flight condition using at least an environmental sensor.

13. The method of claim 10, wherein:
    measuring includes measuring at least a hematological parameter; and
    determining further comprises determining the at least a hematological parameter is associated with the degree of pilot hypoxemia.

14. The method of claim 13, wherein the at least a hematological parameter further comprises a heart rate.

15. The method of claim 10 wherein: measuring includes measuring a blood oxygen level; and determining further comprises determining that the blood oxygen level is associated with the degree of pilot hypoxemia.

16. The method of claim 15, wherein:
    measuring further comprises measuring a heart rate; and
    determination further comprises determining that a combination of blood oxygen level and heart rate is associated with the degree of pilot hypoxemia.

17. The method of claim 10, wherein the degree of pilot hypoxemia further comprises a non-impairing degree of hypoxemia.

18. The method of claim 10, wherein the degree of pilot hypoxemia further comprises an impairing degree of hypoxemia.

19. The method of claim 10, wherein the degree of pilot hypoxemia further comprises a degree of hypoxia associated with an imminent loss of consciousness.

20. The method of claim 10, wherein the training goal is further associated with a duration of hypoxemia and wherein pilot-specific flight guideline is generated further based upon the duration of hypoxemia.

* * * * *